(12) United States Patent
LeMinh et al.

(10) Patent No.: US 7,160,281 B2
(45) Date of Patent: Jan. 9, 2007

(54) ABSORBENT ARTICLE HAVING AN ABSORBENT STRUCTURE SECURED TO A STRETCHABLE COMPONENT OF THE ARTICLE

(75) Inventors: Lisa LeMinh, Neenah, WI (US); Christopher P. Olson, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 307 days.

(21) Appl. No.: 10/690,424

(22) Filed: Oct. 21, 2003

(65) Prior Publication Data
US 2005/0085784 A1  Apr. 21, 2005

(51) Int. Cl.
*A06F 13/20* (2006.01)
(52) U.S. Cl. .................. 604/385.22; 604/385.01; 604/385.23
(58) Field of Classification Search ............... 604/385.01–385.31, 386–402
See application file for complete search history.

(56) References Cited

U.S. PATENT DOCUMENTS

| | | | |
|---|---|---|---|
| 2,931,361 A | 4/1960 | Sostrin | |
| 3,849,241 A | 11/1974 | Butin et al. | |
| 3,978,861 A | 9/1976 | Schaar | |
| 4,036,233 A | 7/1977 | Kozak | |
| 4,050,462 A | 9/1977 | Woon et al. | |
| 4,100,324 A | 7/1978 | Anderson et al. | |
| 4,205,679 A | 6/1980 | Repke et al. | |
| 4,560,372 A | 12/1985 | Pieniak | |
| 4,573,986 A | 3/1986 | Minetola et al. | |
| 4,631,062 A | 12/1986 | Lassen et al. | |
| 4,642,110 A | 2/1987 | Dudek | |
| 4,657,802 A | 4/1987 | Morman | |
| 4,663,220 A | 5/1987 | Wisneski et al. | |
| 4,704,114 A | 11/1987 | Wilson et al. | |
| 4,704,116 A | 11/1987 | Enloe | |
| 4,710,187 A | 12/1987 | Boland et al. | |
| 4,720,415 A | 1/1988 | Vander Wielen et al. | |
| 4,731,066 A | 3/1988 | Korpman | |
| 4,747,846 A | 5/1988 | Bolond et al. | |
| 4,752,349 A | 6/1988 | Gebel | |

(Continued)

FOREIGN PATENT DOCUMENTS

EP   0 603 748 A1   6/1994

(Continued)

OTHER PUBLICATIONS

International Search Report and Written Opinion for International Application No. PCT/US2004/004724, dated Aug. 3, 2004, 12 Pages.

(Continued)

*Primary Examiner*—Tatyana Zalukaeva
*Assistant Examiner*—Melanie J. Hand
(74) *Attorney, Agent, or Firm*—Senniger Powers

(57) ABSTRACT

An absorbent article for personal wear has an outer cover, a bodyside liner adapted for contiguous relationship with the wearer's skin, and an absorbent structure disposed between the liner and the outer cover. The absorbent structure is secured to at least one of the liner and the outer cover within a securement zone. A central portion of the securement zone is disposed generally within a central region of the article and at least one outer portion of the securement zone is disposed longitudinally outward of the central portion thereof.

18 Claims, 11 Drawing Sheets

U.S. PATENT DOCUMENTS

| | | | |
|---|---|---|---|
| 4,753,646 A | 6/1988 | Enloe | |
| 4,756,709 A | 7/1988 | Stevens | |
| 4,808,176 A | 2/1989 | Kielpikowski | |
| 4,834,736 A | 5/1989 | Boland et al. | |
| 4,846,823 A | 7/1989 | Enloe | |
| 4,854,995 A | 8/1989 | Kasper et al. | |
| 4,865,597 A | 9/1989 | Mason, Jr. et al. | |
| 4,874,451 A | 10/1989 | Boger et al. | |
| 4,892,536 A | 1/1990 | DesMarais et al. | |
| 4,935,021 A | 6/1990 | Huffman et al. | |
| 4,938,755 A | 7/1990 | Foreman | |
| 4,940,464 A | 7/1990 | Van Gompel et al. | |
| 4,990,147 A | 2/1991 | Freeland | |
| 5,026,364 A | 6/1991 | Robertson | |
| 5,037,416 A | 8/1991 | Allen et al. | |
| 5,046,272 A | 9/1991 | Vogt et al. | |
| 5,104,116 A | 4/1992 | Pohjola | |
| 5,108,385 A | 4/1992 | Snyder | |
| 5,114,781 A | 5/1992 | Morman | |
| 5,116,662 A | 5/1992 | Morman | |
| 5,151,092 A | 9/1992 | Buell et al. | |
| 5,224,405 A | 7/1993 | Pohjola | |
| 5,226,992 A | 7/1993 | Morman | |
| 5,269,775 A | 12/1993 | Freeland et al. | |
| 5,284,703 A | 2/1994 | Everhart et al. | |
| 5,295,987 A | 3/1994 | Widlund et al. | |
| 5,340,424 A | 8/1994 | Matsushita | |
| 5,350,624 A | 9/1994 | Georger et al. | |
| 5,356,405 A | 10/1994 | Thompson et al. | |
| 5,368,584 A | 11/1994 | Clear et al. | |
| 5,397,316 A | 3/1995 | LaVon et al. | |
| 5,397,317 A | 3/1995 | Thomas | |
| 5,486,166 A | 1/1996 | Bishop et al. | |
| 5,490,846 A | 2/1996 | Ellis et al. | |
| 5,496,429 A | 3/1996 | Hasse | |
| 5,503,076 A | 4/1996 | Yeo | |
| 5,554,143 A | 9/1996 | Roe et al. | |
| 5,567,265 A | 10/1996 | Zajaczkowski | |
| 5,611,790 A | 3/1997 | Osborn, III et al. | |
| 5,624,422 A | 4/1997 | Allen | |
| 5,634,916 A | 6/1997 | Lavon et al. | |
| 5,643,242 A | 7/1997 | Lavon et al. | |
| 5,645,542 A | 7/1997 | Anjur et al. | |
| 5,658,269 A | 8/1997 | Osborn, III et al. | |
| 5,690,627 A | 11/1997 | Clear et al. | |
| 5,695,868 A | 12/1997 | McCormack | |
| 5,766,389 A | 6/1998 | Brandon et al. | |
| 5,804,021 A | 9/1998 | Abuto et al. | |
| 5,817,086 A | 10/1998 | Kling | |
| 5,820,973 A | 10/1998 | Dodge, II et al. | |
| 5,843,056 A | 12/1998 | Good et al. | |
| 5,846,232 A | 12/1998 | Serbiak et al. | |
| 5,873,868 A | 2/1999 | Nakahata | |
| 5,883,028 A | 3/1999 | Morman et al. | |
| 5,925,026 A | 7/1999 | Arteman et al. | |
| 5,928,211 A | 7/1999 | Gustafsson et al. | |
| 5,947,947 A | 9/1999 | Tanzer et al. | |
| 5,957,907 A | 9/1999 | Sauer | |
| 5,964,743 A | 10/1999 | Abuto et al. | |
| 5,997,981 A | 12/1999 | McCormack et al. | |
| 6,049,915 A | 4/2000 | Malowaniec | |
| 6,093,870 A | 7/2000 | Carlsson | |
| 6,103,953 A | 8/2000 | Cree et al. | |
| 6,120,485 A | 9/2000 | Gustafsson et al. | |
| 6,129,720 A | 10/2000 | Blenke et al. | |
| 6,132,411 A | 10/2000 | Huber et al. | |
| 6,149,638 A | 11/2000 | Vogt et al. | |
| 6,149,934 A | 11/2000 | Krzysik et al. | |
| 6,152,906 A | 11/2000 | Faulks et al. | |
| 6,160,197 A | 12/2000 | Lassen et al. | |
| 6,174,303 B1 | 1/2001 | Suprise et al. | |
| 6,193,701 B1 | 2/2001 | Van Gompel et al. | |
| 6,217,563 B1 | 4/2001 | Van Gompel et al. | |
| 6,231,557 B1 | 5/2001 | Krautkramer et al. | |
| 6,262,331 B1 | 7/2001 | Nakahata et al. | |
| 6,264,639 B1 | 7/2001 | Sauer | |
| 6,264,641 B1 | 7/2001 | Van Gompel et al. | |
| 6,312,786 B1 | 11/2001 | Schwinn | |
| 6,362,389 B1 | 3/2002 | McDowall et al. | |
| 6,409,711 B1 | 6/2002 | Jonbrink | |
| 6,413,247 B1 | 7/2002 | Carlucci et al. | |
| 6,461,338 B1 | 10/2002 | Shimoe et al. | |
| 6,482,191 B1 | 11/2002 | Roe et al. | |
| 6,521,811 B1 | 2/2003 | Lassen et al. | |
| 6,552,245 B1 | 4/2003 | Roessler et al. | |
| 6,570,056 B1 | 5/2003 | Tanzer et al. | |
| 6,572,598 B1 | 6/2003 | Ashton et al. | |
| 6,582,414 B1 | 6/2003 | Richardson | |
| 6,610,383 B1 | 8/2003 | Morman et al. | |
| 6,623,465 B1 | 9/2003 | Roe et al. | |
| 6,632,212 B1 | 10/2003 | Morman et al. | |
| 6,645,190 B1 | 11/2003 | Olson et al. | |
| 6,667,424 B1 * | 12/2003 | Hamilton et al. | 604/375 |
| 6,679,869 B1 | 1/2004 | Schlinz et al. | |
| 6,682,512 B1 | 1/2004 | Uitenbroek et al. | |
| 6,695,827 B1 * | 2/2004 | Chen et al. | 604/385.01 |
| 6,702,799 B1 | 3/2004 | Otsubo | |
| 6,702,800 B1 | 3/2004 | Vukos et al. | |
| 6,703,538 B1 | 3/2004 | Lassen et al. | |
| 6,706,028 B1 | 3/2004 | Roe et al. | |
| 6,755,808 B1 | 6/2004 | Balogh et al. | |
| 2002/0025290 A1 | 5/2002 | Zehner et al. | |
| 2002/0052590 A1 | 5/2002 | Zehner et al. | |
| 2002/0111598 A1 | 8/2002 | Vogt et al. | |
| 2002/0165514 A1 | 11/2002 | Datta et al. | |
| 2003/0023213 A1 | 1/2003 | Fernfors et al. | |
| 2004/0013850 A1 | 1/2004 | Kling | |
| 2004/0044323 A1 | 3/2004 | Roessler et al. | |
| 2004/0102749 A1 | 5/2004 | Olson et al. | |
| 2004/0127878 A1 | 7/2004 | Olson et al. | |
| 2004/0127881 A1 | 7/2004 | Stevens et al. | |
| 2005/0124953 A1 * | 6/2005 | Woltman et al. | 604/385.01 |
| 2005/0143710 A1 | 6/2005 | Van Gompel et al. | |
| 2005/0146987 A1 | 7/2005 | Van Gompal et al. | |
| 2005/0148987 A1 | 7/2005 | Van Gompel et al. | |

FOREIGN PATENT DOCUMENTS

| | | |
|---|---|---|
| EP | 605 017 A2 | 7/1994 |
| EP | 0 835 088 B1 | 4/1998 |
| EP | 847 739 A2 | 6/1998 |
| EP | 0 951 886 A1 | 10/1999 |
| EP | 1 201 212 A3 | 5/2002 |
| EP | 1 219 274 A1 | 7/2002 |
| EP | 0 957 868 B1 | 2/2003 |
| EP | 1 310 224 A2 | 5/2003 |
| GB | 2284538 A | 6/1995 |
| GB | 2 305 610 A | 9/1996 |
| GB | 2310606 A | 9/1997 |
| GB | 2325146 A | 11/1998 |
| JP | 2004 195244 A | 7/2004 |
| WO | WO 93/06805 A1 | 4/1993 |
| WO | WO 95/15410 A1 | 5/1995 |
| WO | WO 95/19753 A1 | 7/1995 |
| WO | WO 98/29239 A1 | 7/1998 |
| WO | WO 99/33426 A1 | 7/1999 |
| WO | WO 99/33427 A1 | 7/1999 |
| WO | WO 00/37009 A3 | 6/2000 |
| WO | WO 01/88245 A2 | 11/2001 |
| WO | WO 02/34184 A1 | 5/2002 |
| WO | WO 02/069870 A2 | 9/2002 |
| WO | WO 02/096333 A2 | 12/2002 |
| WO | WO 03/051254 A2 | 6/2003 |
| WO | WO 03/057106 A1 | 7/2003 |

| | | |
|---|---|---|
| WO | WO 04/108041 A1 | 12/2004 |

OTHER PUBLICATIONS

"Polyethylene - Low Density (LDPE) - Material Information," Internet web page "http://www.goodfellow.com/csp/active/STATIC/E/Polyethylene_-_Low_Density.HTML", p. 3, line 1, Goodfellow Corporation, Devon, PA.

* cited by examiner

ABSORBENT ARTICLE HAVING AN ABSORBENT STRUCTURE SECURED TO A STRETCHABLE COMPONENT OF THE ARTICLE

BACKGROUND OF THE INVENTION

The present invention relates generally to absorbent articles intended for personal wear, and more particularly to such absorbent articles having an absorbent structure secured to a stretchable component of the article.

Absorbent articles such as diapers, training pants, incontinence garments, and the like conventionally comprise a liquid permeable body-facing liner, a liquid impermeable outer cover, and an absorbent core (also referred to as an absorbent body or absorbent structure) formed separate from the outer cover and liner and disposed therebetween for taking in and retaining liquid (e.g., urine) exuded by the wearer. In some of these absorbent articles, the outer cover and/or the liner are stretchable to permit some expansion of the article when necessary to provide a better fit on the wearer. During use, the article is subjected to forces such as those generated by loading of the absorbent article and movement of the wearer. These forces can cause the absorbent structure to shift within the absorbent article, to tear, or to otherwise become permanently distorted, all of which reduce the intended absorbent characteristics of the absorbent core and increase the possibility of liquid body exudates leaking from the article.

To this end, it is known to secure a substantial portion of the absorbent structure to the outer cover and/or the liner, such as by adhesive, thermal bonding or ultrasonic bonding, to inhibit the absorbent structure from shifting as the article is subjected to various forces during use. However, securing the absorbent structure to the outer cover and/or liner tends to reduce the stretchability of the substrate to which the absorbent structure is secured, and can impart a measure of inflexibility to the article in the area of securement.

There is need, therefore, to sufficiently secure an absorbent structure to a stretchable component of an absorbent article, such as to the outer cover or bodyside liner, to inhibit permanent distortion of the absorbent structure, while maintaining a desirable level of stretchability of the stretchable component to which the absorbent structure is secured.

SUMMARY OF THE INVENTION

In one embodiment, an absorbent article of the present invention generally has a longitudinal axis, a lateral axis, opposite longitudinal end regions and a central region extending longitudinally between and interconnecting the end regions. The absorbent article generally comprises an outer cover, a bodyside liner adapted for contiguous relationship with the wearer's skin, and an absorbent structure disposed between the bodyside liner and the outer cover. The absorbent structure is secured to at least one of the liner and the outer cover within a securement zone. The securement zone comprises a central portion disposed generally within the central region of the article and having an average width as determined by a Securement Zone Measurement Method. At least one outer portion of the securement zone is disposed longitudinally outward of the central portion of the securement zone and has an average width as determined by the Securement Zone Measurement Method. The average width of the central portion of the securement zone is substantially greater than the average width of the at least one outer portion of the securement zone.

In another embodiment, an absorbent article generally comprises an outer cover, a bodyside liner adapted for contiguous relationship with the wearer's skin, and an absorbent structure disposed between the bodyside liner and the outer cover and having longitudinally opposite ends and laterally opposite side edges. The absorbent structure extends generally from within a first end region of the article through a center region to within a second end region of the article is secured to at least one of the liner and the outer cover within a securement zone having laterally opposite side boundaries. The securement zone comprises at least in part a central portion wherein the side boundaries of the securement zone are disposed laterally within at least about one inch (2.54 centimeters) of the respective side edges of the absorbent structure. The side boundaries of any portion of the securement zone disposed longitudinally outward of the central portion thereof are spaced laterally inward of the respective side edges of the absorbent structure a distance greater than about one inch (2.54 centimeters).

In general, an absorbent article according to yet another embodiment comprises an outer cover, a bodyside liner adapted for contiguous relationship with the wearer's skin, and an absorbent structure disposed between the bodyside liner and the outer cover and having longitudinally opposite ends and laterally opposite side edges. The absorbent structure extends generally from within a first end region of the article through a center region to within a second end region of the article and is secured to at least one of the liner and the outer cover within a securement zone. The securement zone comprises at least in part a central portion having an average width as determined by a Securement Zone Measurement Method that is at least about 20 percent of a width of the absorbent structure at the central portion. Any portion of the securement zone disposed longitudinally outward of the central portion thereof having an average width as determined by the Securement Zone Measurement Method of less than about 20 percent of the width of the absorbent structure at the longitudinally outward portion of the securement zone.

In still another embodiment, an absorbent article for personal wear generally comprises an outer cover, a bodyside liner adapted for contiguous relationship with the wearer's skin, and an absorbent structure disposed between the bodyside liner and the outer cover and having longitudinally opposite ends and laterally opposite side edges. The absorbent structure extends generally from within a first end region of the article through a center region to a second end region of the article and is secured to at least one of the liner and the outer cover within a securement zone. At least a portion of the securement zone has laterally opposite side boundaries and longitudinally opposite end boundaries. The side boundaries of the at least a portion of the securement zone are within at least about one inch of the respective side edges of the absorbent structure. One end boundary of the at least a portion of the the securement zone is longitudinally spaced from the first end of the absorbent article a distance in the range of about 20 percent to about 45 percent of a length of the absorbent article. The opposite end boundary of the at least a portion of the absorbent article is longitudinally spaced from the second end of the absorbent article a distance in the range of about 20 percent to about 50 percent of the length of the absorbent article.

Other features of the invention will be in part apparent and in part pointed out hereinafter.

BRIEF DESCRIPTION OF THE DRAWINGS

Corresponding reference characters indicate corresponding parts throughout the several views of the drawings.

Definitions

Figure 1:
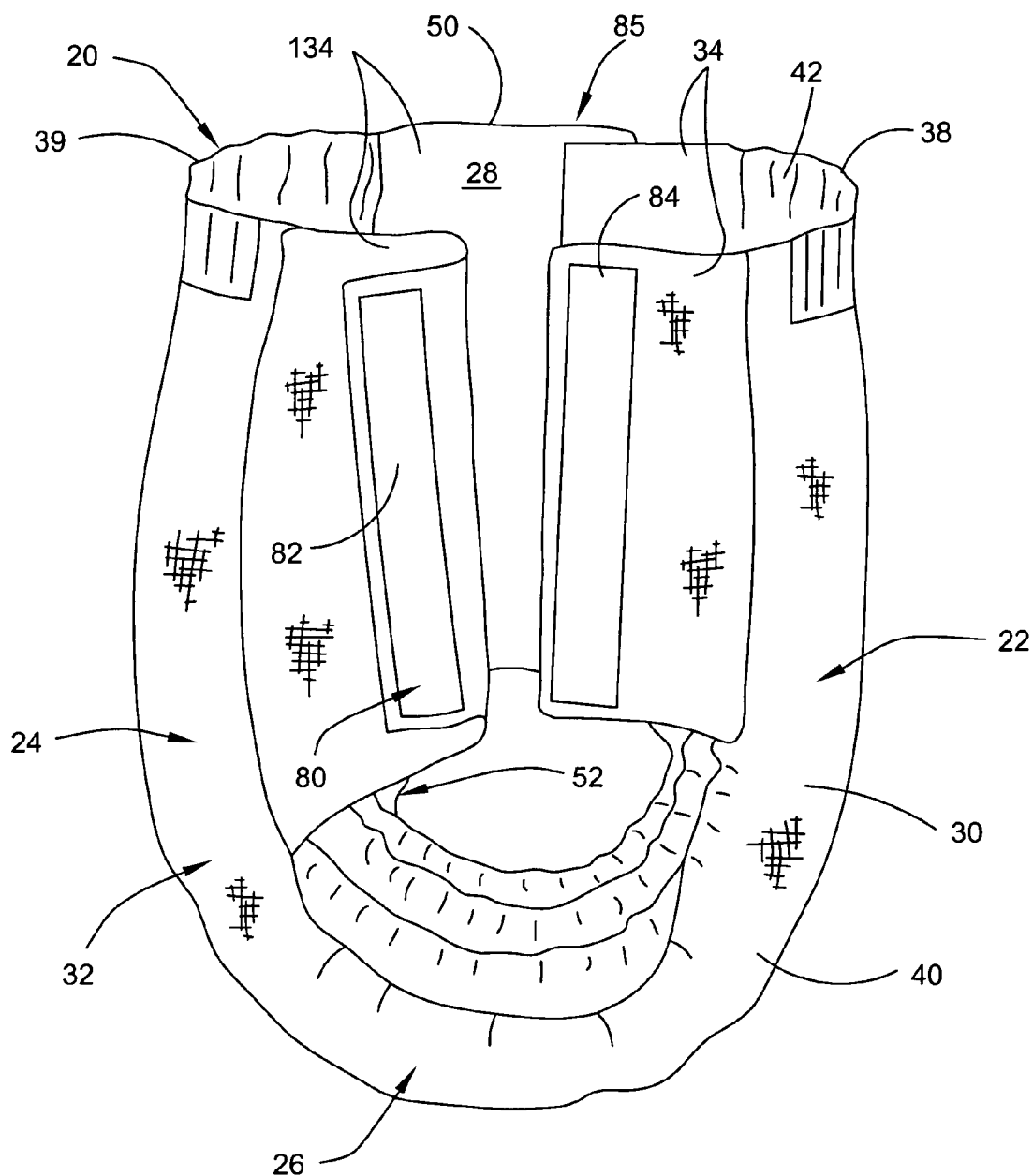
FIG. 1 is a side perspective of an article of the present invention shown in the form of a pair of training pants having a mechanical fastening system fastened on one side of the training pants and unfastened on the opposite side thereof.

Within the context of this specification, each term or phrase below includes the following meaning or meanings:

"Attached" refers to the joining, adhering, connecting, bonding, or the like, of two elements. Two elements will be considered to be attached to one another when they are attached directly to one another or indirectly to one another, such as when each is directly attached to intermediate elements.

"Hydrophilic" describes fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90 degrees are designated "wettable" or hydrophilic, and fibers having contact angles greater than 90 degrees are designated "nonwettable" or hydrophobic.

"Layer" when used in the singular can have the dual meaning of a single element or a plurality of elements.

"Liquid impermeable," when used in describing a layer or multi-layer laminate means that liquid body waste, such as urine, will not pass through the layer or laminate, under ordinary use conditions, in a direction generally perpendicular to the plane of the layer or laminate at the point of liquid contact.

"Liquid permeable" refers to any material that is not liquid impermeable.

"Meltblown" refers to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameters. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al. Meltblown fibers are microfibers which may be continuous or discontinuous, are generally smaller than about 0.6 denier, and are generally self bonding when deposited onto a collecting surface. Meltblown fibers used in the present invention are preferably substantially continuous in length.

"Non-woven" and "non-woven web" refer to materials and webs of material which are formed without the aid of a textile weaving or knitting process.

"Superabsorbent" refers to a water-swellable, water-insoluble organic or inorganic material capable, under the most favorable conditions, of absorbing at least about fifteen times its weight and, more desirably, at least about thirty times its weight in an aqueous solution containing 0.9 weight percent sodium chloride. The superabsorbent materials can be natural, synthetic and modified natural polymers and materials, or a combination of such materials. In addition, the superabsorbent materials can be inorganic materials, such as silica gels, or organic compounds such as cross-linked polymers.

"Surge Layer" refers to a layer typically comprised of non-woven materials capable of absorbing a large surge of liquid and releasing it slowly to another layer or layers.

"Thermoplastic" describes a material which softens when exposed to heat and which substantially returns to a non-softened condition when cooled to room temperature.

DETAILED DESCRIPTION OF THE PREFERRED EMBODIMENTS

Referring now to the drawings and in particular to FIG. 1, an absorbent article of the present invention is shown therein in the form of children's toilet training pants and is indicated in its entirety by the reference numeral 20. The absorbent article 20 may or may not be disposable, which refers to articles that are intended to be discarded after a limited period of use instead of being laundered or otherwise conditioned for reuse. It is understood that the present invention is suitable for use with various other absorbent articles intended for personal wear, including but not limited to diapers, feminine hygiene products, incontinence products, medical garments, surgical pads and bandages, other personal care or health care garments, and the like without departing from the scope of the present invention.

By way of illustration only, various materials and methods for constructing training pants such as the pants 20 of FIG. 1 are disclosed in PCT Patent Application WO 00/37009 published Jun. 29, 2000 by A. Fletcher et al; U.S. Pat. No. 4,940,464 issued Jul. 10, 1990 to Van Gompel et al.; and U.S. Pat. No. 5,766,389 issued Jun. 16, 1998 to Brandon et al., which are incorporated herein by reference.

The pair of training pants 20 is illustrated in FIG. 1 in a partially fastened condition and comprises longitudinal end regions, otherwise referred to herein as a front waist region 22 and a back waist region 24, and a center region, otherwise referred to herein as a crotch region 26, extending longitudinally between and interconnecting the front and back waist regions. The pants 20 also has an inner surface 28 adapted (e.g., positioned relative to the other components of the pants 20) for contiguous relationship with the wearer, and an outer surface 30 opposite the inner surface. The front and back waist regions 22, 24 comprise those portions of the pants 20, which when worn, wholly or partially cover or encircle the waist or mid-lower torso of the wearer. The crotch region 26 generally comprises that portion of the pants 20 which, when worn, is positioned between the legs of the wearer and covers the lower torso and crotch of the wearer. With additional reference to FIGS. 2 and 3, the training pants 20 has a pair of laterally opposite side edges 36 and a pair of longitudinally opposite waist edges (broadly, longitudinal ends), respectively designated front waist edge 38 and back waist edge 39.

Figure 2:
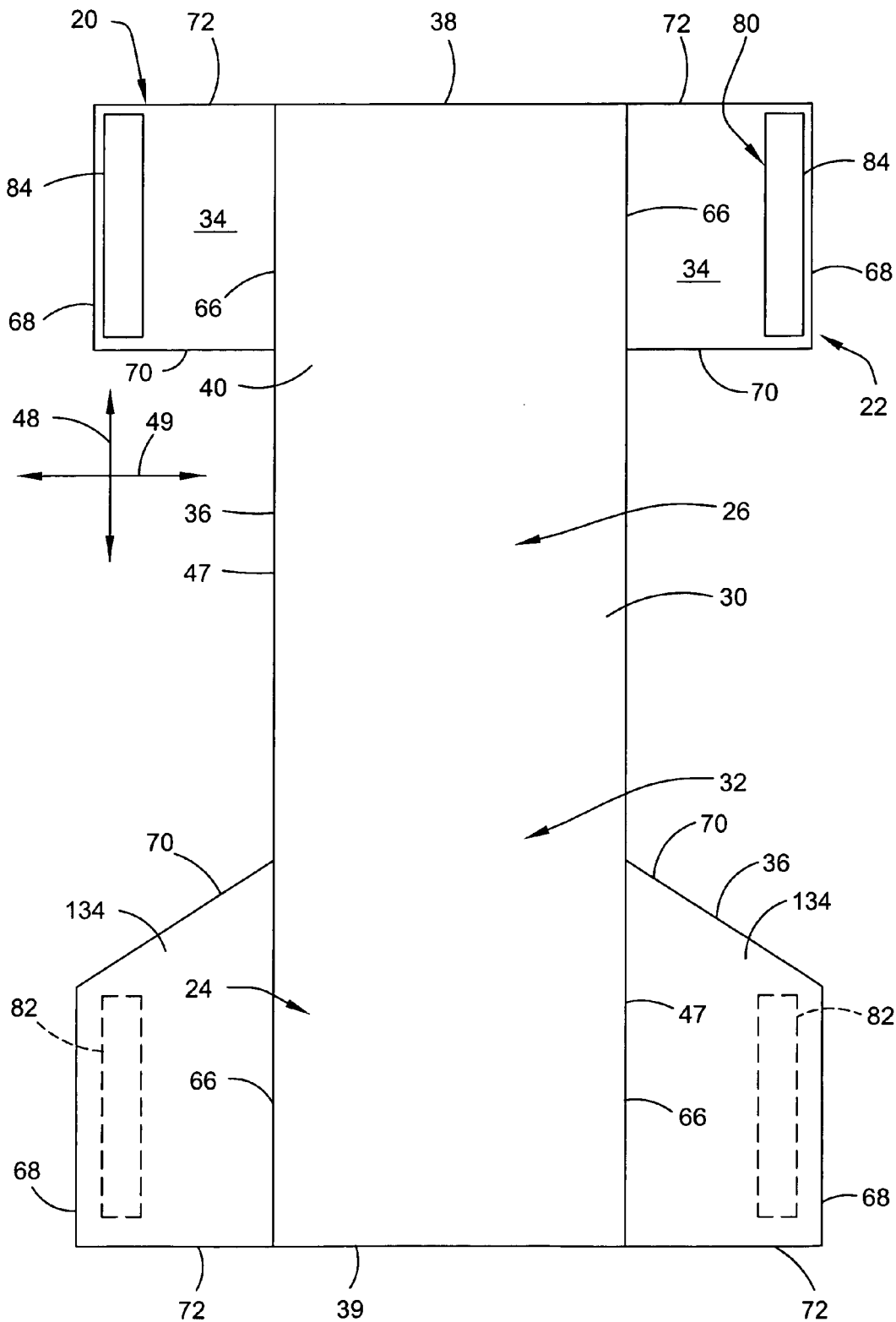
FIG. 2 is a bottom plan view of the training pants of FIG. 1 with the pants in an unfastened, unfolded and laid flat condition, and showing the surface of the training pants that faces away from the wearer.
Figure 3:
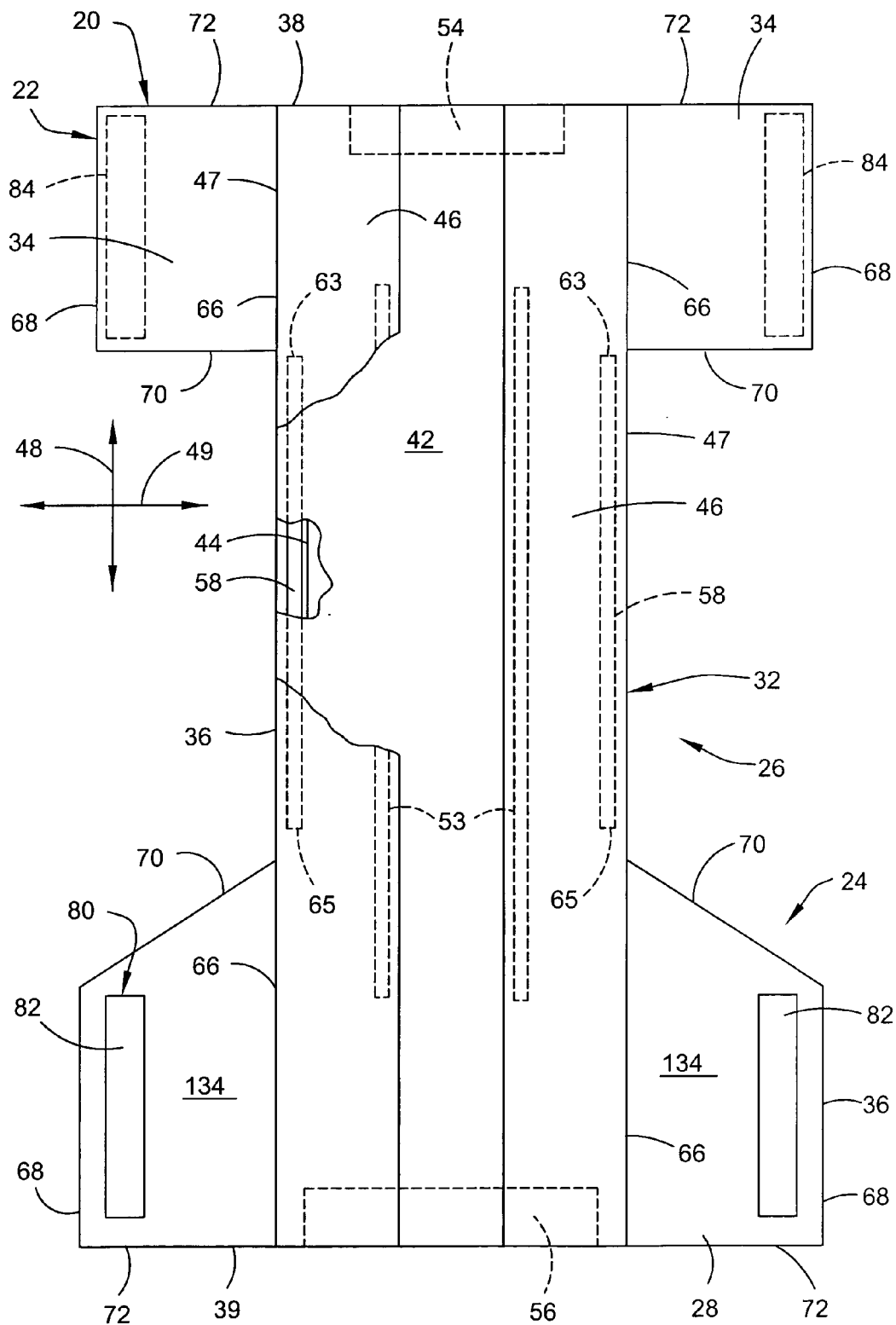
FIG. 3 is a top plan view similar to FIG. 2 showing the surface of the training pants that faces the wearer when worn and with portions cut away to show underlying features.
Figure 10:
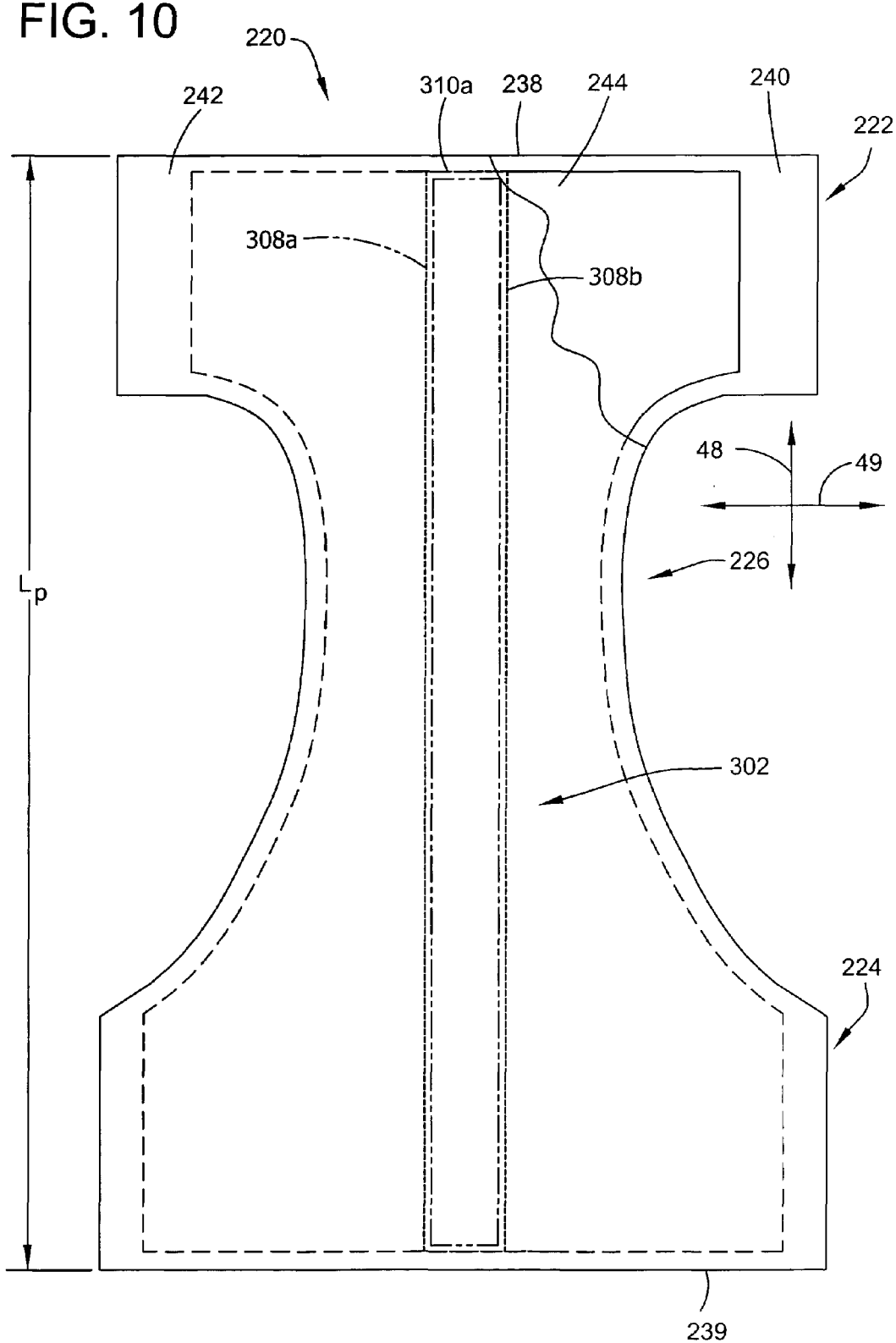
FIG. 10 is a top plan view of a second embodiment of a pair of training pants showing the surface of the training pants that faces the wearer and further showing an absorbent structure of the pants secured to an outer cover thereof within a securement zone.
Figure 11:
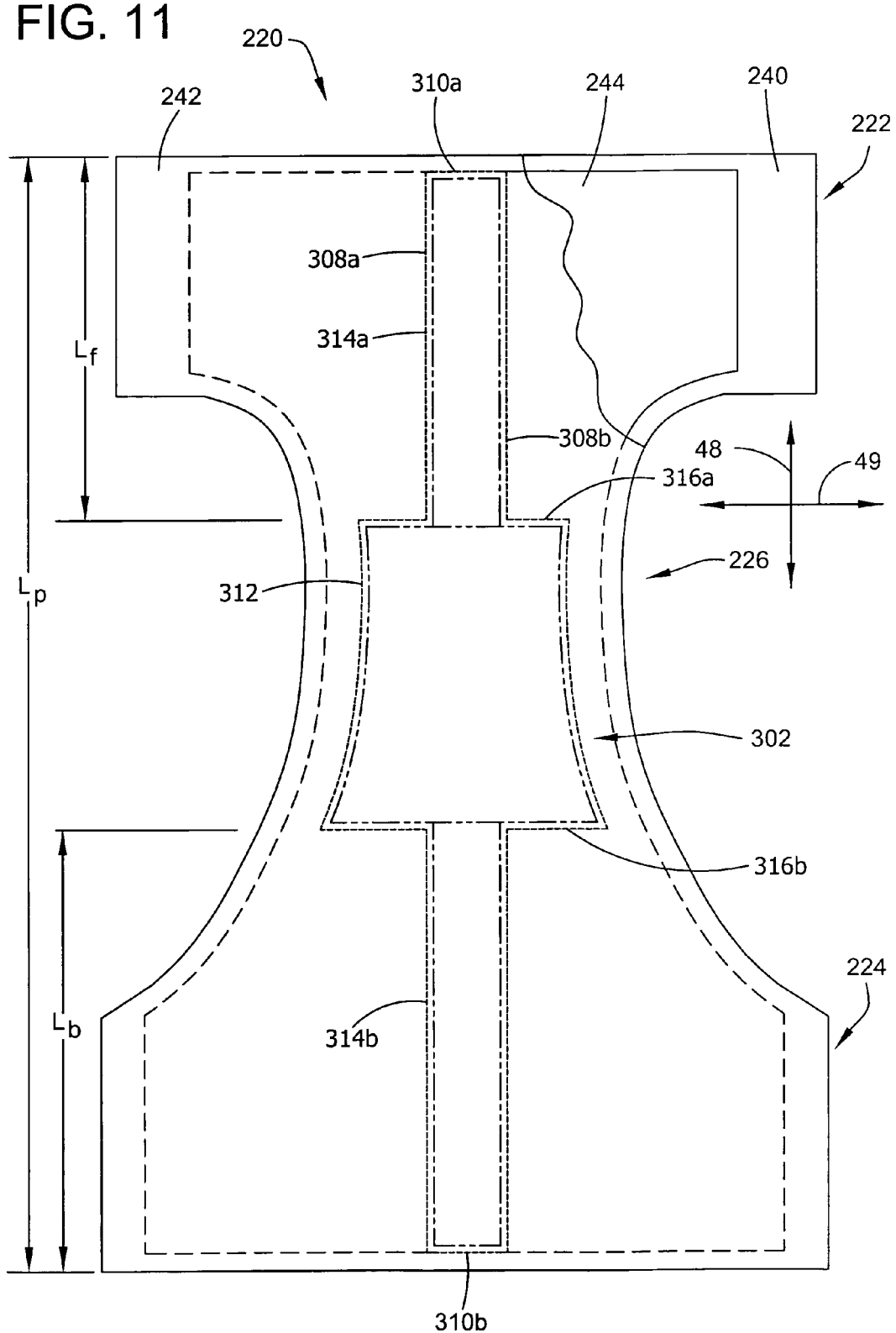
FIG. 11 is a top plan view similar to FIG. 10 showing another embodiment of a securement zone.

The illustrated pants 20 comprises a central absorbent assembly, generally indicated at 32, having a pair of laterally opposite front side panels 34 extending laterally outward at the front waist region 22 and a pair of laterally opposite back side panels 134 extending laterally outward at the back waist region 24. The central absorbent assembly 32 is illustrated in FIGS. 2 and 3 as being generally rectangular. However, it is contemplated that the absorbent assembly 32, may be other than rectangular, such as hourglass shaped as shown in the embodiments of FIGS. 10 and 11, T-shaped, I-shaped, and the like without departing from the scope of this invention.

Still referring to FIGS. 1–3, the central absorbent assembly 32 comprises an outer cover 40 and a bodyside liner 42 (FIGS. 1 and 3) attached to the outer cover in a superposed relation therewith by adhesives, ultrasonic bonds, thermal bonds or other conventional techniques. The liner 42 is suitably adapted, i.e., positioned relative to the other components of the pants 20, for contiguous relationship with the wearer's skin during wear of the pants. The absorbent assembly 32 also comprises an absorbent structure 44 (FIG. 3) disposed between the outer cover 40 and the bodyside liner 42 for absorbing liquid body exudates exuded by the wearer, and a pair of containment flaps 46 (FIG. 3) secured to the bodyside liner 42 for inhibiting the lateral flow of body exudates.

The central absorbent assembly 32 of the illustrated embodiment has longitudinal ends which form portions of the front and back waist edges 38 and 39, and opposite side edges 47 which form portions of the side edges 36 of the training pants 20 (FIGS. 2 and 3). For further reference, arrows 48 and 49 depict the orientation of the longitudinal axis and the transverse or lateral axis, respectively, of the training pants 20.

With the training pants 20 in the fastened position as partially illustrated in FIG. 1, the front and back side panels 34, 134 are connected together by a fastening system 80 to define a three-dimensional pants configuration having a waist opening 50 and a pair of leg openings 52. The front and back side panels 34 and 134, upon wearing of the pants 20, thus comprise the portions of the training pants 20 which are positioned on the hips of the wearer. The front and back waist edges 38 and 39 of the training pants 20 are configured to encircle the waist of the wearer and together define a waist opening 50 (FIG. 1) of the pants. Portions of the side edges 36 in the crotch region 26 generally define leg openings 52 of the pants 20.

A flap elastic member 53 (FIG. 3) can be operatively joined with each containment flap 46 in any suitable manner as is well known in the art. The elasticized containment flaps 46 define a partially unattached edge which assumes an upright configuration in at least the crotch region 26 of the training pants 20 to form a seal against the wearer's body. The containment flaps 46 can be located along the side edges 36 of the pants 20, and can extend longitudinally along the entire length of the absorbent assembly 32 or may only extend partially along the length of the absorbent assembly. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pants 20 also suitably includes a front waist elastic member 54 (FIG. 3), a rear waist elastic member 56, and leg elastic members 58, as are known to those skilled in the art. The waist elastic members 54 and 56 can be operatively joined to the outer cover 40 and/or the bodyside liner 42 along the opposite waist edges 38 and 39, and can extend over part or all of the waist edges. The leg elastic members 58 can be operatively joined to the outer cover 40 and/or the bodyside liner 42 along the opposite side edges 36 and positioned in the crotch region 26 of the training pants 20. The leg elastic members 58 can be longitudinally aligned along each side edge 47 of the absorbent assembly 32. Each leg elastic member 58 has a front terminal point 63 and a back terminal point 65, which represent the longitudinal ends of the elastic gathering caused by the leg elastic members.

The flap elastic members 53, the waist elastic members 54 and 56, and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic retractive forces are imparted to the substrate. In one particular embodiment, for example, the leg elastic members 58 comprise a plurality of dry-spun coalesced multifilament spandex elastomeric threads sold under the trade name LYCRA® and available from E. I. Du Pont de Nemours and Company, Wilmington, Del., U.S.A.

The side panels 34, 134 can be permanently bonded along seams 66 to the central absorbent assembly 32 in the respective front and back waist regions 22 and 24. More particularly, as seen best in FIGS. 2 and 3, the front side panels 34 can be permanently bonded to and extend transversely outward beyond the side edges 47 of the absorbent assembly 32 at the front waist region 22, and the back side panels 134 can be permanently bonded to and extend transversely outward beyond the side edges of the absorbent assembly at the back waist region 24. The side panels 34 and 134 may be bonded to the absorbent assembly 32 using attachment means known to those skilled in the art such as adhesive, thermal or ultrasonic bonding.

Alternatively, the side panels 34 and 134 can be formed as an integral portion of a component of the absorbent assembly 32 as shown in the embodiments of FIGS. 10 and 11. For example, the side panels 34, 134 can comprise a generally wider portion of the outer cover 40, the bodyside liner 42, and/or another component of the absorbent assembly 32. The front and back side panels 34 and 134 can be permanently bonded together to form the three-dimensional configuration of the pants 20, or be releasably connected with one another such as by the fastening system 80 of the illustrated embodiment.

The front and back side panels 34, 134 each have an outer edge 68 spaced laterally from the seam 66, a leg end edge 70 disposed toward the longitudinal center of the training pants 20, and a waist end edge 72 disposed toward a longitudinal end of the training pants. The leg end edge 70 and waist end edge 72 extend from the side edges 47 of the absorbent assembly 32 to the outer edges 68. The leg end edges 70 and outer edges 68 of the side panels 34 and 134 form part of the side edges 36 of the training pants 20. The leg end edges 70 of the illustrated embodiment are suitably curved and/or angled relative to the transverse axis 49 to provide a better fit around the wearer's legs. However, it is understood that only one of the leg end edges 70 may be curved or angled, such as the leg end edge of the back waist region 24, or neither of the leg end edges may be curved or angled, without departing from the scope of this invention. The waist end edges 72 are suitably parallel to the transverse axis 49. The waist end edges 72 of the front side panels 34 form part of the front waist edge 38 of the training pants 20, and the waist end edges 72 of the back side panels 134 form part of the back waist edge 39 of the pants.

The side panels 34, 134 suitably, although not necessarily, comprise an elastic material capable of stretching in a direction generally parallel to the transverse axis 49 of the training pants 20. Suitable elastic materials, as well as one process of incorporating elastic side panels into training pants, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular embodiments, the elastic material may comprise a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; European Patent Application No. EP 0 217 032 published on Apr. 8, 1987 in the name of Taylor et al.; and PCT application WO 01/88245 in the name of Welch et al.; all of which are incorporated herein by reference. Alternatively, the side panel material may comprise other woven or non-woven materials, such as those described later herein as being suitable for construction of the outer cover 40 and/or the bodyside liner 42; mechanically pre-strained composites; or stretchable but inelastic materials.

The fastening system 80 comprises laterally opposite first fastening components 82 adapted for refastenable engagement to corresponding second fastening components 84. In one embodiment, a front or outer surface of each of the fastening components 82, 84 comprises a plurality of engaging elements. The engaging elements of the first fastening components 82 are adapted to repeatedly engage and disengage corresponding engaging elements of the second fastening components 84 to releasably secure the pants 20 in its three-dimensional configuration.

The fastening components 82, 84 can comprise any refastenable fasteners suitable for absorbent articles, such as adhesive fasteners, cohesive fasteners, mechanical fasteners, or the like. In particular embodiments the fastening components comprise mechanical fastening elements for improved performance. Suitable mechanical fastening elements can be provided by interlocking geometric shaped materials, such as hooks, loops, bulbs, mushrooms, arrowheads, balls on stems, male and female mating components, buckles, snaps, or the like.

In the illustrated embodiment, the first fastening components 82 comprise loop fasteners and the second fastening components 84 comprise complementary hook fasteners. Alternatively, the first fastening components 82 may comprise hook fasteners and the second fastening components 84 may comprise complementary loop fasteners. In another embodiment, the fastening components 82, 84 can comprise interlocking similar surface fasteners, or adhesive and cohesive fastening elements such as an adhesive fastener and an adhesive-receptive landing zone or material; or the like. Although the training pants 20 illustrated in FIG. 1 show the back side panels 134 overlapping the front side panels 34 upon connection thereto, which is convenient, the training pants 20 can also be configured so that the front side panels overlap the back side panels when connected. One skilled in the art will recognize that the shape, density and polymer composition of the hooks and loops may be selected to obtain the desired level of engagement between the fastening components 82, 84. A more aggressive hook material may comprise a material with a greater average hook height and/or a greater percentage of directionally-aligned hooks. When engaged, the fastening components 82, 84 of the illustrated embodiment define refastenable engagement seams 85 (FIG. 1).

The outer cover 40 suitably comprises a material which is substantially liquid impermeable. The outer cover 40 can be a single layer of liquid impermeable material, but more suitably comprises a multi-layered laminate structure in which at least one of the layers is liquid impermeable. For instance, the outer cover 40 can include a liquid permeable outer layer and a liquid impermeable inner layer that are suitably joined together by a laminate adhesive, ultrasonic bonds, thermal bonds, or the like. Suitable laminate adhesives, which can be applied continuously or intermittently as beads, a spray, parallel swirls, or the like, can be obtained from Bostik Findley Adhesives, Inc., of Wauwatosa, Wis., U.S.A., or from National Starch and Chemical Company, Bridgewater, N.J. U.S.A. The liquid permeable outer layer can be any suitable material and is desirably one that provides a generally cloth-like texture. One example of such a material is a 20 gsm (grams per square meter) spunbond polypropylene nonwoven web. The outer layer may also be made of those materials of which the liquid permeable bodyside liner 42 is made. While it is not a necessity for the outer layer to be liquid permeable, it is suitable that it provides a relatively cloth-like texture to the wearer.

The inner layer of the outer cover 40 can be both liquid and vapor impermeable, or it may be liquid impermeable and vapor permeable. The inner layer can be manufactured from a thin plastic film, although other flexible liquid impermeable materials may also be used. The inner layer, or the liquid impermeable outer cover 40 when a single layer, prevents waste material from wetting articles, such as bed sheets and clothing, as well as the wearer and caregiver. A suitable liquid impermeable film for use as a liquid impermeable inner layer, or a single layer liquid impermeable outer cover 40, is a 0.02 millimeter polyethylene film commercially available from Pliant Corporation of Schaumburg, Ill., U.S.A.

More suitably, the outer cover 40 is stretchable, and even more suitably the outer cover is elastic. As used herein, the term "stretchable" refers to a material that may be extensible and/or elastic. That is, the material may be extended, deformed or the like, without breaking, and may or may not significantly retract after removal of an extending force. The term "elastic" refers to that property of a material where upon removal of an elongating force, the material is capable of recovering to substantially its unstretched size and shape or the material exhibits a significant retractive force. The term "extensible" refers to that property of a material where upon removal of an elongating force, the material experiences a substantially permanent deformation or the material does not exhibit a significant retractive force.

For example, the outer cover 40 may be constructed of a single layer, multiple layers, laminates, spunbond fabrics, films, meltblown fabrics, elastic netting, microporous web, bonded carded webs or foams comprised of elastomeric or polymeric materials. Elastomeric non-woven laminate webs can include a non-woven material joined to one or more gatherable non-woven webs, films, or foams. Stretch Bonded Laminates (SBL) and Neck Bonded Laminates (NBL) are examples of elastomeric composites. Non-woven fabrics are any web of material which has been formed without the use of textile weaving processes which produce a structure of individual fibers that are interwoven in an identifiable repeating manner.

Examples of suitable materials are spunbond-meltblown fabrics, spunbond-meltblown-spunbond fabrics, spunbond fabrics, or laminates of such fabrics with films, foams, or other nonwoven webs. Elastomeric materials may include cast or blown films, foams, or meltblown fabrics composed of polyethylene, polypropylene, or polyolefin copolymers, as well as combinations thereof. The elastomeric materials may include PEBAX elastomer (available from AtoChem located in Philadelphia, Pa.), HYTREL elastomeric polyester (available from E. I. DuPont de Nemours of Wilmington, Del.), KRATON elastomer (available from Shell Chemical Company of Houston, Tex.), or strands of LYCRA elastomer (available from E. I. DuPont de Nemours of Wilmington, Del.), or the like, as well as combinations thereof. The outer cover 40 may include materials that have elastomeric properties through a mechanical process, printing process, heating process, or chemical treatment. For examples such materials may be apertured, creped, neck-stretched, heat activated, embossed, and micro-strained; and may be in the form of films, webs, and laminates.

In particularly suitable embodiments of the invention, the outer cover 40 may comprise a 0.4 ounces per square yard (osy) (13.6 grams per square meter (gsm)) basis weight layer of G2760 KRATON elastomer strands adhesively laminated with a 0.3 gsm layer of adhesive between two facings. Each facing can be composed of a thermal point bonded bicomponent spunbond non-woven fibrous web having a 0.7 osy (23.7 gsm) basis weight. The adhesive is similar to an adhesive which is supplied by AtoFindley Adhesive and designated as H2525 A, and the elastomer strands are placed and distributed to provide approximately 12 strands of KRATON elastomer per inch (2.54 cm) of lateral width of the outer cover 40.

Alternatively, the outer cover 40 may comprise a woven or non-woven fibrous web layer which has been totally or partially constructed or treated to impart the desired levels of liquid impermeability to selected regions that are adjacent or proximate the absorbent structure. For example, the outer cover 40 may comprise a gas-permeable, non-woven fabric layer laminated to a polymer film layer which may or may not be gas-permeable. Other examples of fibrous, cloth-like outer cover 40 materials can comprise a stretch thinned or stretch thermal laminate material composed of a 0.6 mil (0.015 mm) thick polypropylene blown film and a 0.7 osy (23.8 gsm) polypropylene spunbond material (2 denier fibers).

The outer cover 40 is suitably sized (e.g., in length and width) larger than the absorbent structure 44 to extend outward beyond the periphery thereof. For example, the outer cover 40 may extend outward beyond the absorbent structure 44 periphery a distance in the range of about 1.3 centimeters to about 2.5 centimeters (about 0.5 to 1 inch). Also, while the absorbent structure 44 of the illustrated embodiment is generally rectangular in accordance with the shape of the absorbent assembly 32, it is contemplated that the absorbent assembly 32 (and hence the outer cover 40) may be other than rectangular, such as hourglass-shaped as shown in the embodiments of FIGS. 10 and 11, I-shaped, T-shaped and the like.

The bodyside liner 42 is suitably compliant, soft-feeling, and non-irritating to the wearer's skin. The bodyside liner 42 is also sufficiently liquid permeable to permit liquid body exudates to readily penetrate through its thickness to the absorbent structure 44. A suitable bodyside liner 42 may be manufactured from a wide selection of web materials, such as porous foams, reticulated foams, apertured plastic films, woven and non-woven webs, or a combination of any such materials. For example, the bodyside liner 42 may comprise a meltblown web, a spunbonded web, or a bonded-carded-web composed of natural fibers, synthetic fibers or combinations thereof. The bodyside liner 42 may be composed of a substantially hydrophobic material, and the hydrophobic material may optionally be treated with a surfactant or otherwise processed to impart a desired level of wettability and hydrophilicity.

The bodyside liner 42 may also be stretchable, and more suitably it may be elastic. Suitable elastomeric materials for construction of the bodyside liner 42 can include elastic strands, LYCRA elastics, cast or blown elastic films, non-woven elastic webs, meltblown or spunbond elastomeric fibrous webs, as well as combinations thereof. Examples of suitable elastomeric materials include KRATON elastomers, HYTREL elastomers, ESTANE elastomeric polyurethanes (available from B.F. Goodrich and Company of Cleveland, Ohio), or PEBAX elastomers.

As an additional example, in one embodiment the bodyside liner 42 suitably comprises a non-woven, spunbond polypropylene fabric composed of about 2 to 3 denier fibers formed into a web having a basis weight of about 12 gsm which is necked to approximately 40 percent of its original width. Strands of about 9 gsm KRATON G2760 elastomer material placed eight strands per inch (2.54 cm) are adhered to the necked spunbond material. The fabric is surface treated with an operative amount of surfactant, such as about 0.6 percent AHCOVEL Base N62 surfactant, available from ICI Americas, a business having offices of Wilmington, Del., U.S.A. The surfactant can be applied by any conventional means, such as spraying, printing, brush coating or the like.

The bodyside liner 42 and outer cover 40 are suitably attached to one another. For example, the bodyside liner 42 may be directly attached to the outer cover 40 by affixing the bodyside liner 42 directly thereto, or it may be indirectly attached to the outer cover by affixing the bodyside liner to intermediate components which in turn are affixed to the outer cover. The bodyside liner 42 and the outer cover 40 can, for example, be attached to each other along at least a portion of their periphery by adhesive, ultrasonic bonding, thermal bonding or other suitable attachment means known in the art.

The absorbent structure 44 is suitably compressible, conformable and capable of absorbing and retaining liquid body exudates released by the wearer. It should be understood that, for purposes of this invention, the absorbent body structure may comprise a single, integral piece of material, or alternatively it may comprise a plurality of individual separate pieces of material which are operatively assembled together.

In a particularly suitable embodiment, the absorbent structure 44 comprises a matrix of hydrophilic fibers, and more suitably cellulosic fluff, such as wood pulp fluff, and superabsorbent particles. One suitable pulp fluff is identified with the trade designation CR1654, commercially available from U.S. Alliance, Childersburg, Ala., U.S.A., and is a bleached, highly absorbent sulfate wood pulp containing primarily soft wood fibers and about 16 percent hardwood fibers. As an alternative to wood pulp fluff, synthetic fibers, polymeric fibers, meltblown fibers, short cut homofil bicomponent synthetic fibers, or other natural fibers may be used without departing from the scope of this invention.

Suitable superabsorbent materials can be selected from natural, synthetic, and modified natural polymers and materials. The superabsorbent materials can be inorganic materials, such as silica gels, or organic compounds, such as crosslinked polymers, for example, sodium neutralized polyacrylic acid. Suitable superabsorbent materials are available from various commercial vendors, such as Dow Chemical Company of Midland, Mich., U.S.A., and Stockhausen Inc., Greensboro, N.C., U.S.A.

The superabsorbent material can be substantially homogeneously mixed with the hydrophilic fibers or non-uniformly mixed therewith. The fibers and superabsorbent material may also be selectively placed into desired zones of the absorbent structure 44 to better contain and absorb body exudates. The concentration of the superabsorbent particles can also vary through the thickness of the absorbent core 44. Alternatively, the absorbent structure 44 can comprise a laminate of fibrous webs and superabsorbent material or other suitable means of maintaining a superabsorbent material in a localized area.

As a general rule, the superabsorbent material is present in the absorbent structure 44 in an amount of from 0 to about 90 weight percent based on total weight of the absorbent assembly. The absorbent structure 44 suitably has a density within the range of about 0.10 to about 0.35 grams per cubic centimeter and may or may not be wrapped or encompassed by a suitable tissue wrap for maintaining the integrity and/or shape of the absorbent structure.

Figure 4:
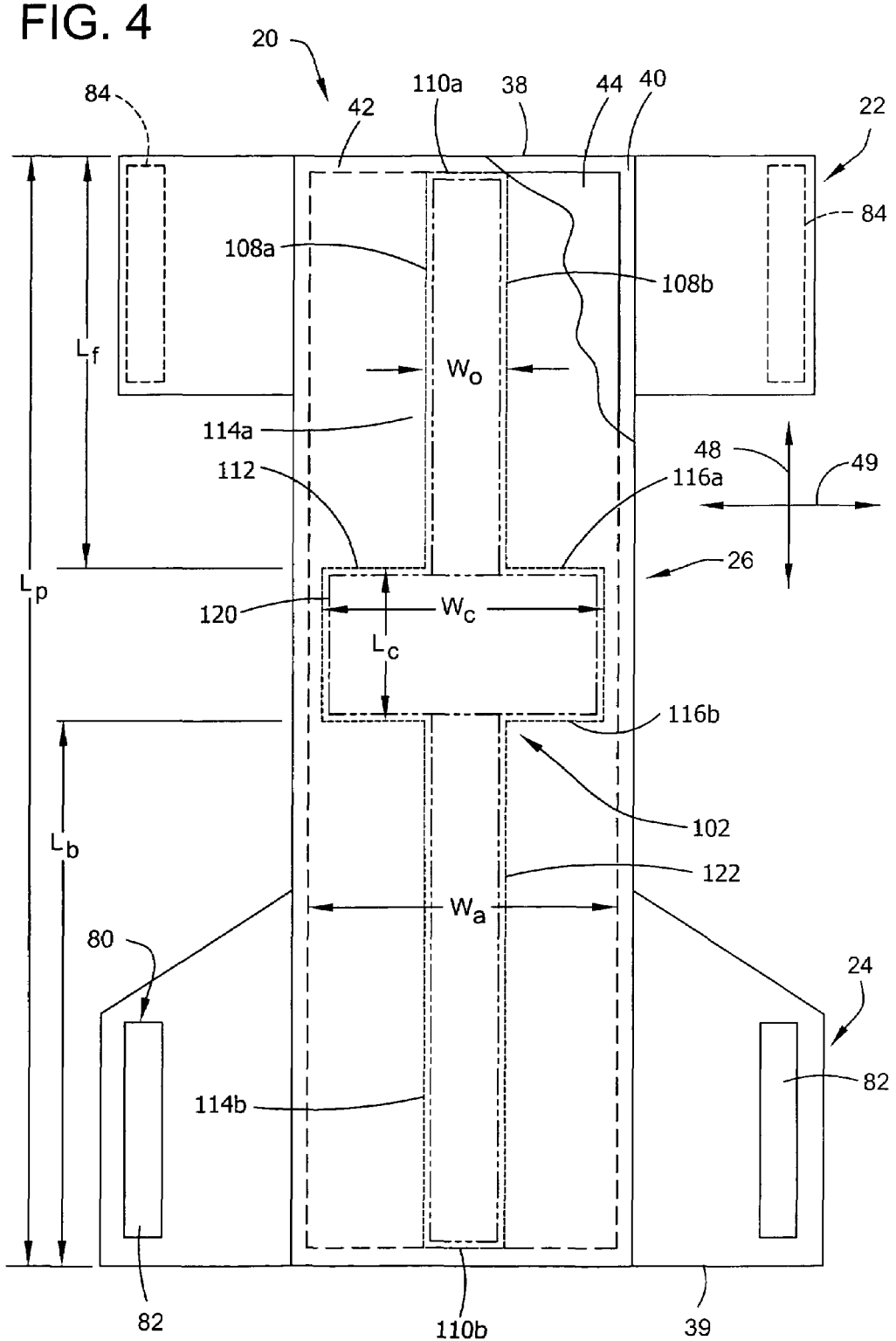
FIG. 4 is a top plan view similar to FIG. 3 showing an absorbent structure of the pants secured to an outer cover thereof within a securement zone.

With particular reference now to FIG. 4, the absorbent structure 44 is suitably secured to the outer cover 40 within in a securement zone, generally indicated at 102 with small dashed lines. As used herein, the securement zone 102 generally refers to a bounded area within which the absorbent structure 44 is secured to the outer cover 40, such as by adhesive or other suitable securement techniques as described later herein. Alternatively, or additionally, the absorbent structure 44 may be secured to the bodyside liner 42 or other components of the pants 20, the securement zone then being a bounded region within which the absorbent structure is collectively secured to the outer cover 40, the bodyside liner 42 and/or other components of the pants 20. The securement zone 102 has laterally opposite side boundaries 108a, 108b defined by the laterally outermost securement of the absorbent structure 44 to the outer cover 40 along the length of the absorbent structure. The securement zone 102 also has longitudinally opposite end boundaries 110a, 110b defined by the longitudinally outermost securement of the absorbent structure 44 to the outer cover 40 across the width of the absorbent structure. For example, in FIG. 4 the end boundaries 110a, 110b of the securement zone 102 are generally in registry with the longitudinal ends of the absorbent structure 44.

A central portion 112 of the securement zone 102 is disposed longitudinally generally within the crotch region 26 of the pants 20 and has an average width $W_C$, as determined by a Securement Zone Measurement Method described later herein. Outer portions 114a, 114b of the securement zone 102 extend longitudinally outward relative to the central portion 112 thereof generally toward the ends of the absorbent structure 44, and hence respectively toward the front and back regions 22, 24 of the pants 20. Each outer portion 114a, 114b of the securement zone 102 has a respective average width $W_O$ as determined by the Securement Zone Measurement Method. The average width $W_C$ of the central portion 112 of the securement zone 102 is suitably greater than the average width $W_O$ of each outer portion 114a, 114b thereof so that the central portion of the securement zone defines longitudinally opposite end boundaries 116a, 116b spaced longitudinally inward from the ends of the pants 20 and an average length $L_C$ (as determined by the Securement Zone Measurement Method) between the longitudinal end boundaries of the central portion of the securement zone.

Suitably, the laterally opposite side boundaries 108a, 108b of the securement zone 102 at the central portion 112 thereof are disposed laterally (i.e., as determined parallel to the lateral axis 49 of the pants 20) inward from the side edges of the absorbent structure 44 a distance of less than or equal to about one inch (25.4 mm). For example, a width $W_A$ of the portion of the absorbent structure 44 corresponding to the central portion 112 of the securement zone 102 is suitably in the range of about 50 mm to about 100 mm whereas the average width $W_C$ of the central portion of the securement zone is suitably in the range of about 10 mm to about 100 mm. Thus, while the laterally opposite side boundaries 108a, 108b of the securement zone 102 at the central portion 112 thereof are illustrated in FIG. 4 as being spaced laterally inward of the side edges of the absorbent structure 44, it will be understood that the side boundaries of the securement zone may be spaced from the absorbent structure side edges a distance other than as shown in FIG. 4, or they may be in registry with (e.g., generally lie on) the absorbent structure side edges and remain within the scope of this invention.

The laterally opposite side boundaries 108a, 108b of the securement zone 102 at the outer portions 114a, 114b thereof are suitably spaced laterally from the side edges (e.g., as determined parallel to the lateral axis 49 of the pants 20) of the absorbent structure 44 generally within the respective front and back regions 22, 24 of the pants 20 a distance greater than about one inch (25.4 mm). For example, the width $W_A$ of the absorbent structure 44 generally at the front and back regions 22, 24 of the pants 20 may suitably be in the range of about 100 mm to about 200 mm, whereas the average width $W_O$ of each of the outer portions 114a, 114b of the securement zone 102 may suitably be in the range of about 5 mm to about 30 mm, and more suitably about 10 mm to about 20 mm.

Still referring to FIG. 4, the pants 20 has a length $L_p$ measured from one longitudinal end (e.g., front waist edge 38) of the pants to the opposite longitudinal end (e.g., back waist edge 39) thereof. The average length $L_C$ of the central portion 112 of the securement zone 102 (e.g., between the end boundaries 116a, 116b of the central portion) may suitably be in the range of about 5 to about 50 percent of the length $L_p$ of the pants, more suitably in the range of from about 10 to about 30 percent thereof, and still more suitably in the range of about 10 to about 20 percent thereof.

As a further example, the width $W_C$ of the central portion 112 of the securement zone 102 may suitably be at least about 20 percent of the width $W_A$ of the portion of the absorbent structure 44 corresponding to the central portion of the securement zone (e.g., as determined in a direction parallel to the lateral axis 49 of the pants 20), and may more suitably be in the range of about 20 percent to about 80 percent thereof, and still more suitably in the range of about 20 percent to about 60 percent thereof. The width $W_O$ of the outer portions 114a, 114b of the securement zone 102, e.g., toward the front and back regions 22, 24 of the pants 20, may suitably be less than about 20 percent of the width $W_A$ of the absorbent structure 44 at the portions of the absorbent structure corresponding to the the outer portions of the securement zone.

The central portion 112 of the securement zone 102 shown in FIG. 4 is also suitably sized (e.g., in length $L_C$) and/or longitudinally positioned at the crotch region 26 of the pants 20 such that the longitudinal end boundary 116b nearer the back waist edge 39 of the pants 20 can be spaced longitudinally therefrom a distance $L_b$ in the range of about 20 to about 50 percent of the length $L_p$ of the pants 20, more suitably in the range of about 30 to about 50 percent thereof, and still more suitably in the range of about 40 to about 50 percent thereof. As an example, where the length $L_p$ of the pants 20 is about 500 mm, the longitudinal end boundary 116b of the central portion 112 nearest the back waist edge 39 may be spaced longitudinally therefrom a distance $L_b$ in the range of about 100 mm to about 250 mm, and more suitably in the range of about 200 mm to about 250 mm.

The longitudinal end boundary 116a of the central portion 112 of the securement zone 102 nearest the front waist edge 38 of the pants 20 can be suitably spaced longitudinally therefrom a distance $L_f$ in the range of about 20 to about 45 percent of the length $L_p$ of the pants, more suitably in the range of about 25 to about 40 percent thereof, and still more suitably in the range of about 35 to about 40 percent thereof. As an example, where the length $L_p$ of the pants 20 is about 500 mm, the longitudinal end boundary 116a of the central portion 112 nearest the front waist edge 38 may be spaced longitudinally therefrom a distance $L_F$ in the range of about 100 mm to about 225 mm, and more suitably in the range of about 175 mm to about 200 mm. Thus, it will be recognized that in certain configurations the position of the central portion 112 of the securement zone 102 may be generally biased toward the front waist edge 38 of the pants 20.

As described previously and illustrated in FIG. 4, the absorbent structure 44 can be secured within the securement zone 102 to the outer cover 40 of the pants 20. Alternatively, or additionally, the absorbent structure 44 may be secured within the securement zone 102 to the bodyside liner 42 or to other components of the pants 20. For example, the absorbent structure 44 may be secured to the outer cover 40 of the pants 20 within the central portion 112 of the securement zone 102 and to the bodyside liner 42 of the pants within the outer portions 114a, 114b of the securement zone, or vice versa, or within both the outer portions and the central portion of the securement zone. In such an embodiment, the outer portions 114a, 114b of the securement zone 102 may be defined by a relatively narrow strip along which the absorbent structure 44 is secured to the respective outer cover 40 or bodyside liner 42 along the length of the absorbent structure, or by a pair of discrete strips (not shown) spaced longitudinally from each other in correspondence with the length $L_C$ of the central portion 112 of the securement zone.

The outer portions 114a, 114b of the securement zone 102 illustrated in FIG. 4 extend longitudinally from the central portion 112 thereof to the respective longitudinal ends of the absorbent structure 44. However, it is contemplated that one or both of the outer portions 114a, 114b of the securement zone 102 need not extend to the respective ends of the absorbent structure 44 to remain within the scope of the invention. In such an embodiment, the securement zone 102 has a length less than the full length of the absorbent structure 44. It is also contemplated that the outer portions 114a, 114b of the securement zone 102 may not overlap or abut the central portion 112 of the securement zone, and may instead be spaced longitudinally therefrom so that there is a gap between the outer portions and the central portion of the securement zone wherein the absorbent structure is free from securement to the outer cover 40 and bodyside liner 42. Alternatively, the outer portions 114a, 114b may be omitted altogether whereby the securement zone 102 is defined solely by what is described herein and shown in the drawings as the central portion 112 thereof.

The absorbent structure 44 is suitably secured to the outer cover 40, the bodyside liner 42 and/or other components of the pants 20 within the securement zone 102 by adhesive. For illustrative purposes only throughout the various drawings, regions in which adhesive secures the absorbent structure 44 to the outer cover 40 and/or bodyside liner 42, such as the central and outer adhesive regions 120 and 122 shown in FIG. 4 and described later herein, are delineated by long/short dashed lines. Also for illustrative purposes only throughout the various drawings, where the side boundaries 108a, 108b and end boundaries 110a, 110b of the securement zone 102 are intended to lie in registry with the lines used to delineate the adhesive regions 120, 122, the securement zone boundaries are shown slightly off-set from the lines used to delineate such adhesive regions.

One suitable adhesive is a meltblown adhesive available from Bostik Findley Inc. of Wauwatosa, Wis., U.S.A., under the designation H2343-01. Other examples of suitable adhesives include, without limitation, the 2300 Series of adhesives by Bostik Findley Adhesives, the 2400 Series of adhesives by Bostik Findley Adhesives, and HL1258 available from Fuller Co. of St. Paul, Minn. Other suitable adhesives include styrene block copolymer based adhesives and olefin based adhesives.

The adhesive is conventionally applied to the outer cover 40, bodyside liner 42 and/or the absorbent structure 44 by melt blowing the adhesive through a melt blowing system (not shown) comprising a suitable dispensing apparatus having at least one nozzle through which one or more streams of adhesive is blown onto the respective component by a heated gas, such as air. The blown adhesive is generally fibrous and may include a single fiber or filament or a plurality of fibers or filaments. Thus, the resulting series of fibers may be continuous filaments or may be discrete fibers. As an example, the adhesive fibers may have a diameter in the range of about 5 microns to about 120 microns, and more suitably about 7 microns to about 30 microns.

Accordingly, in one embodiment the melt-blown adhesive fibers bond to the absorbent structure 44 and to the outer cover 40 and/or bodyside liner 42 of the pants 20 to thereby secure the absorbent structure to the outer cover and/or liner. The adhesive fibers may be applied to the absorbent structure 44, the outer cover 40 and/or the bodyside liner 42 in one or more patterns which are known to those skilled in the art. For example, the adhesive may be applied in swirl patterns, slot coated patterns, air laid or spot coated patterns, and/or continuous bead line patterns.

In the illustrated embodiment of FIG. 4, the central portion 112 of the securement zone 102 is defined by the adhesive region 120 wherein adhesive is distributed generally uniformly throughout the central portion of the securement zone. However, it is understood, depending on the pattern of application used, that the adhesive may secure only a small fraction of the surface area of the absorbent structure 44 to the outer cover 40 (and/or the bodyside liner 42) within the central portion 112 of the securement zone 102. For example, where a swirl pattern or dispersed spray pattern is used to apply the adhesive, much of the absorbent structure 44 within the securement zone does not have adhesive applied thereto and is therefore free from securement to the outer cover 40 and bodyside liner 42. The outer portions 114a, 114b of the securement zone 102 are defined by the adhesive region 122 wherein adhesive is distributed generally uniformly along a relatively narrow strip extending the length of the absorbent structure 44. However, only a small fraction of the surface area of the absorbent structure 44 may actually be secured to the outer cover 40 (and/or the bodyside liner 42) within the outer portions 114a, 114b such as in a manner similar to the central portion 112 of the securement zone 102.

As an example, the amount of surface area of the absorbent structure 44 secured to the outer cover 40 (and/or the bodyside liner 42) within the securement zone is suitably in the range of about 1.5 percent to about 100 percent of the surface area of one side of the absorbent structure, more suitably in the range of about 3 percent to about 50 percent, still more suitably in the range of about 3 percent to about 12 percent, and even more suitably in the range of about 3 percent to about 5 percent. Where the absorbent structure 44 is secured to the bodyside liner 42, the amount of adhesive used should be sufficient to provide the desired level of securement, but should be low enough to avoid excessively inhibiting the flow of liquid from the bodyside liner 42 to the absorbent structure.

Figure 5:
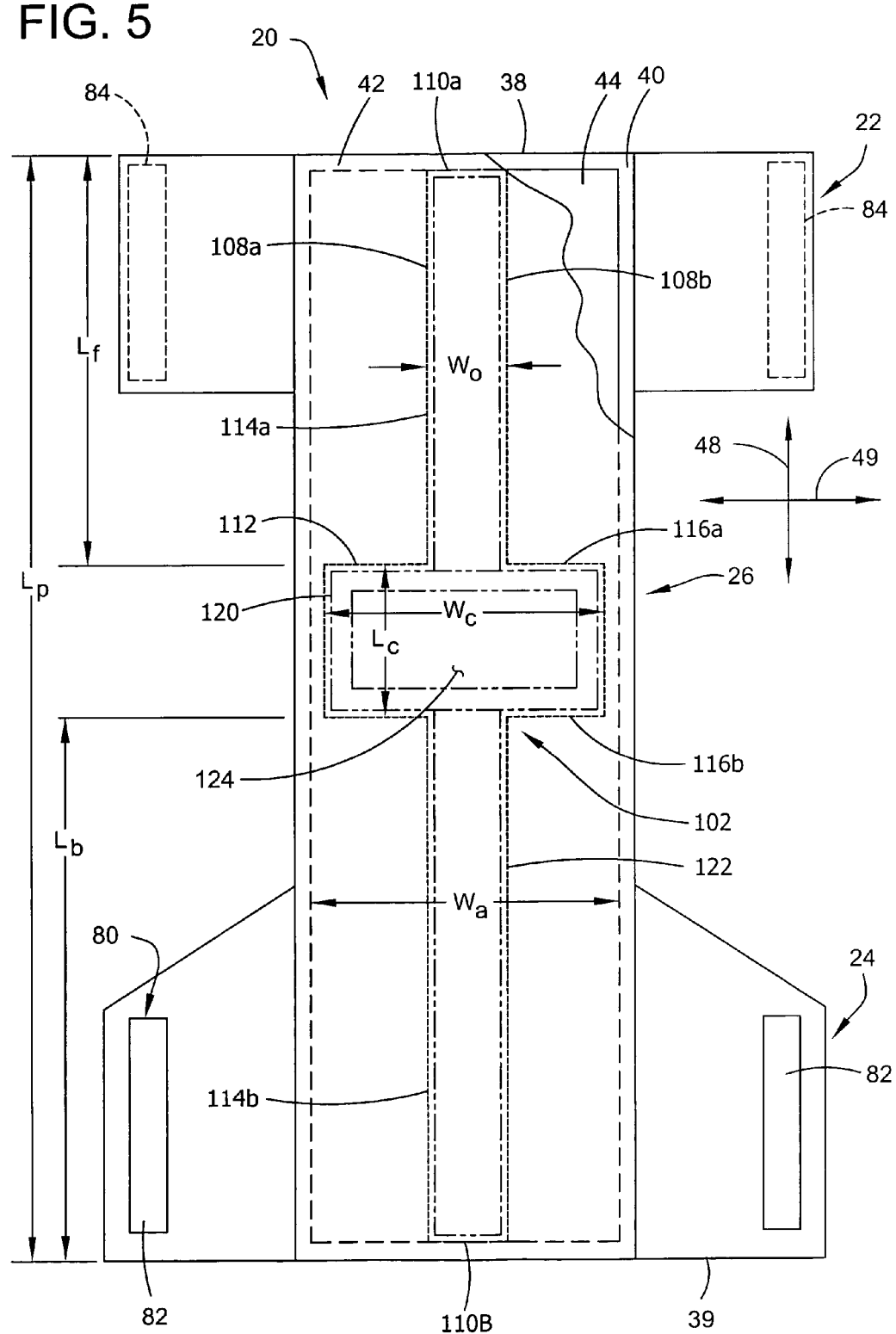
FIG. 5 is a top plan view similar to FIG. 4 showing a second embodiment of a securement zone.
Figure 6:
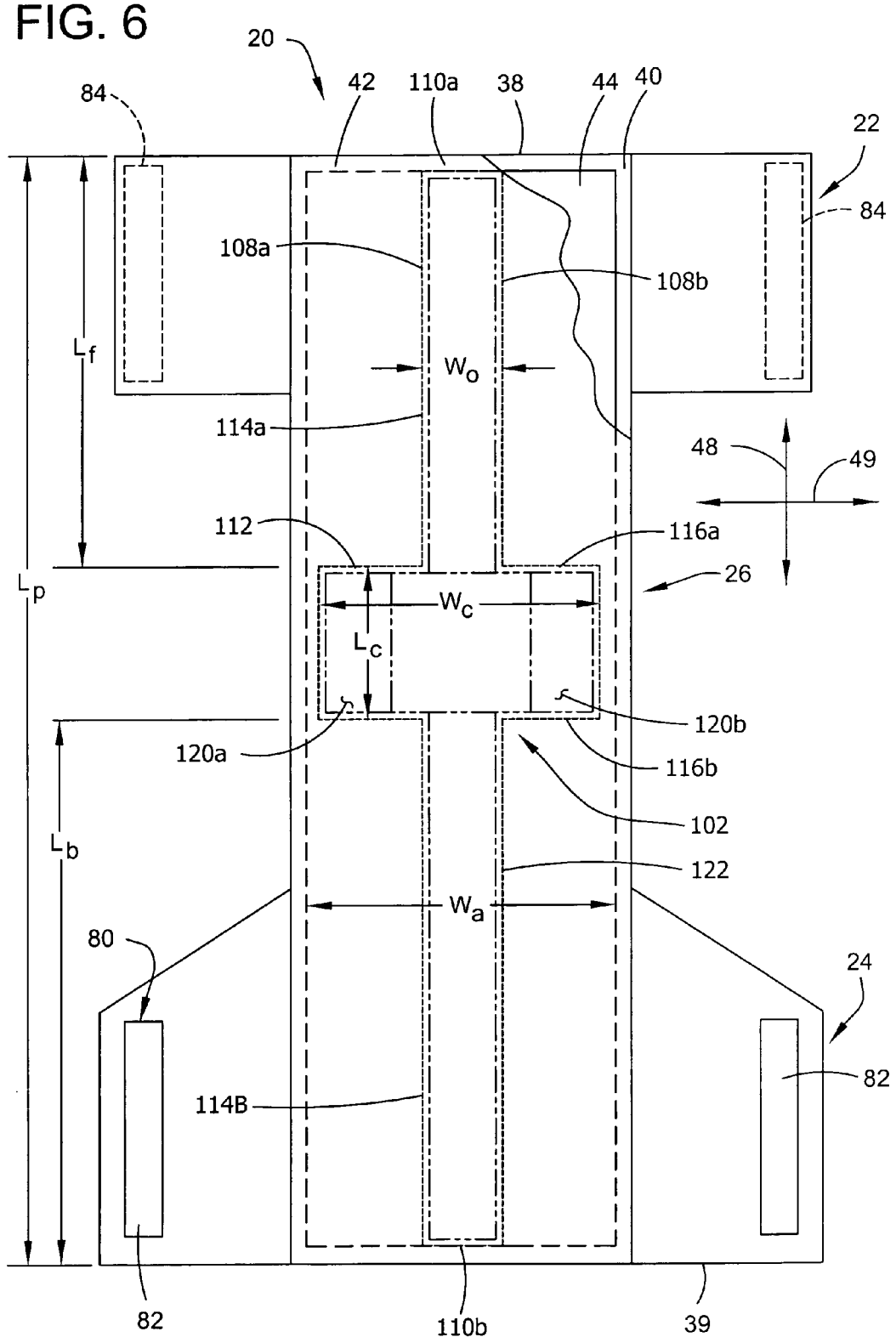
FIG. 6 is a top plan view similar to FIG. 4 showing a third embodiment of a securement zone.

It is further contemplated that securement of the absorbent structure 44 to the outer cover 40 need not be uniform throughout the securement zone. For example, as shown in FIG. 5, an inner region 124 of the central portion 112 of the securement zone 102 may be free from adhesive so that the absorbent structure 44 is free from securement to the outer cover 40 and bodyside liner 42 at the inner region. Thus, the absorbent structure is secured to the outer cover 40 and/or bodyside liner 42 only within a surrounding rectangular region which defines the central portion 112 of the securement zone 102. FIG. 6 illustrates another embodiment in which the central portion 112 of the securement zone 102 is defined by a pair of laterally spaced adhesive regions 120a, 120b, with the lateral space therebetween being free from adhesive such that the absorbent structure is free from securement to the outer cover 40 and bodyside liner 42 therebetween. However, in each of the embodiments of FIGS. 5 and 6, the laterally and longitudinally outermost locations of securement between the absorbent structure 44 and the outer cover 40 (and/or the bodyside liner 42) still define a securement zone 102 having the same shape and size as the securement zone shown in FIG. 4.

It is contemplated that other suitable adhesives may be used instead of, or in addition to, the adhesive described above, and that the adhesive may be applied in another known manner. Alternatively, or additionally, the absorbent structure 44 may be secured to the outer cover 40 and/or the bodyside liner 42 within the securement zone 102 by ultrasonic bonding, thermal bonding or other suitable securement techniques known to those skilled in the art.

In use, e.g., during wear, the pair of training pants 20 is subjected to forces generated by movement of the wearer, including both compressive and shearing forces which act on the lateral side edges 36 of the pants (and hence the lateral side edges of the absorbent structure 44). The central portion 112 of the securement zone 102 suitably secures the absorbent structure 44 to the outer cover 40 and/or bodyside liner 42 near the side edges of the absorbent structure, generally within the crotch region 26 of the pants 20 (e.g., where the forces are primarily concentrated), to inhibit the side edges of the absorbent structure against rolling inward at the crotch region. The narrower outer portions 114a, 114b of the securement zone 102 (i.e., relative to the width $W_A$ of the absorbent structure 44) reduces the loss of stretchability of the outer cover 40 and/or bodyside liner 42 to which the absorbent structure 44 is secured, particularly near the front and back waist regions 22, 24 of the pants 20 where more lateral stretching is needed to allow for a more comfortable fit on the wearer.

Figure 7:
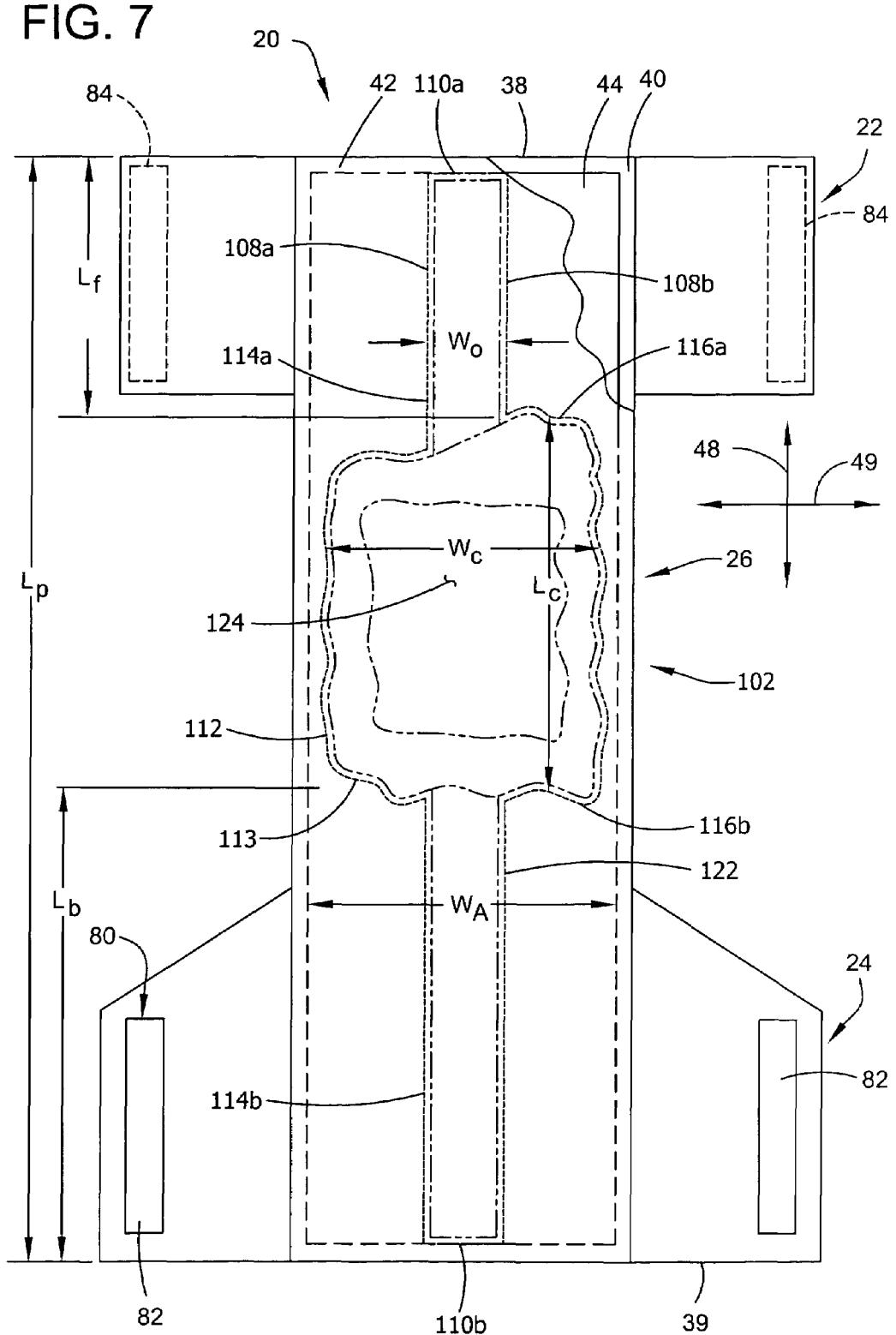
FIG. 7 is a top plan view similar to FIG. 4 showing a fourth embodiment of a securement zone.
Figure 8:
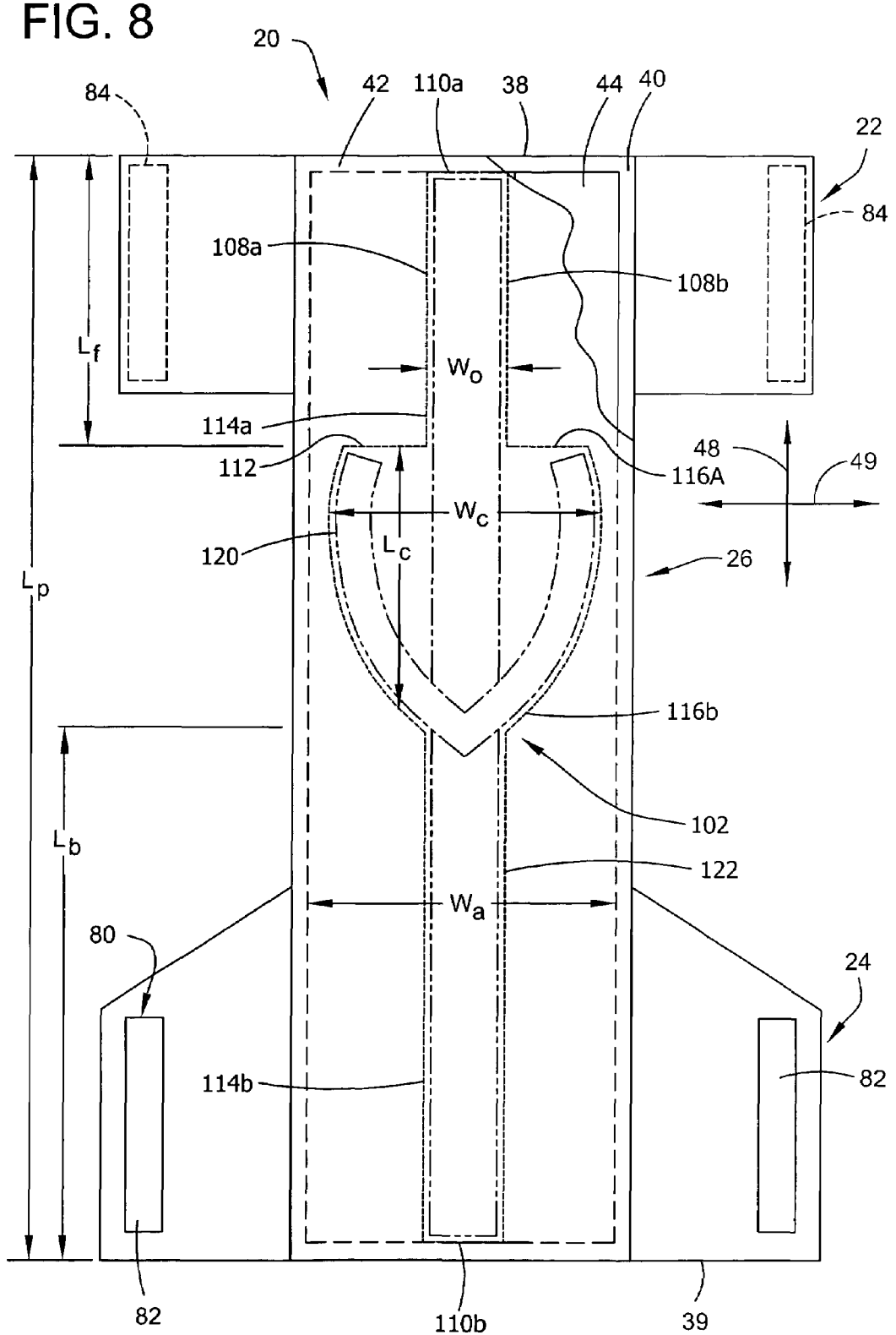
FIG. 8 is a top plan view similar to FIG. 4 showing a fifth embodiment of a securement zone.
Figure 9:
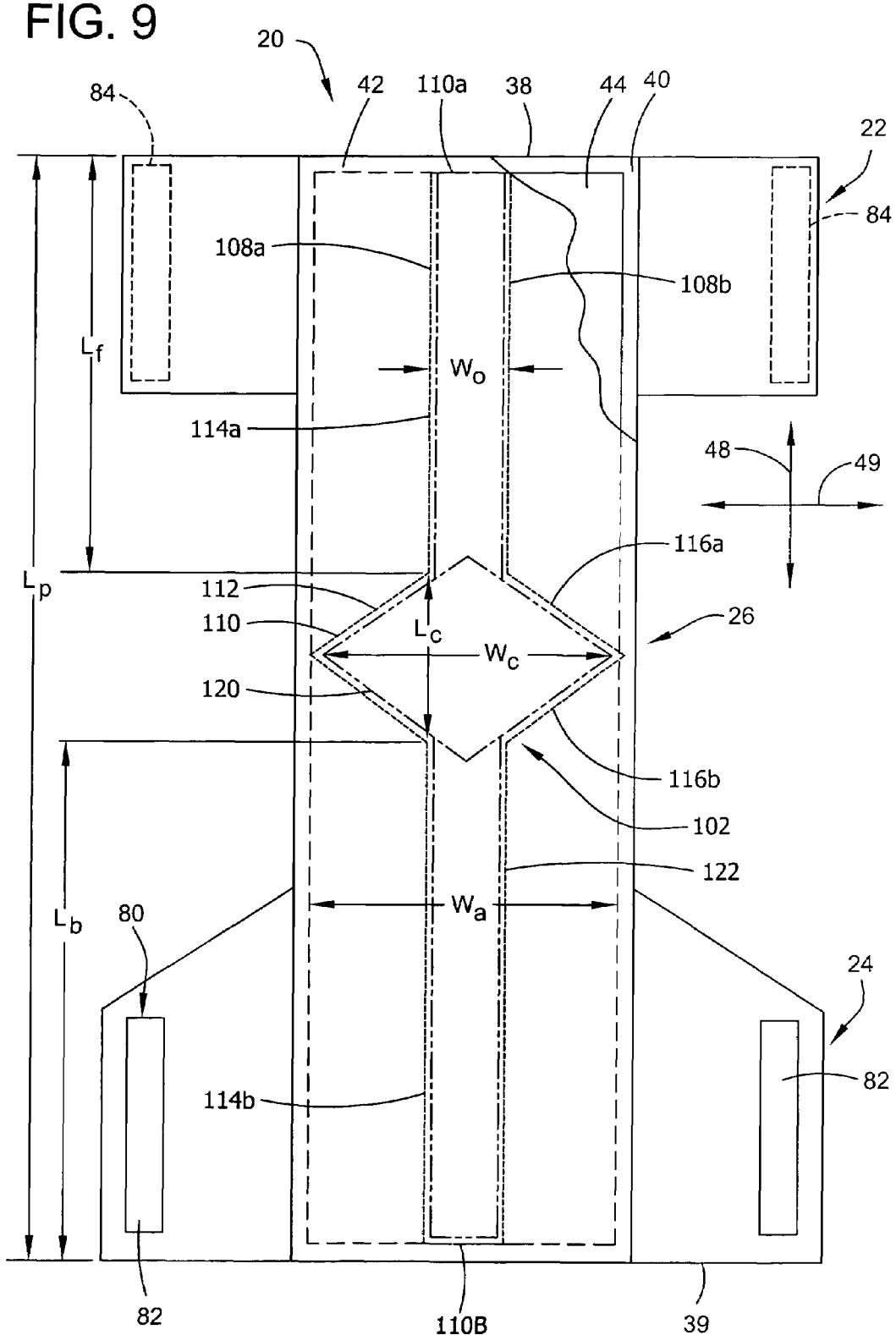
FIG. 9 is a top plan view similar to FIG. 4 showing a sixth embodiment of a securement zone.

With reference now to FIGS. 7–9, it is understood that the securement zone 102 may be shaped other than as shown in FIGS. 4–6 without departing from the scope of this invention. For example, in the illustrated embodiment of FIG. 7, the laterally opposite side boundaries 108a, 108b of the securement zone 102 at the central portion 112 thereof, and the longitudinally opposite end boundaries 116a, 116b of the central portion, are substantially non-linear. The absorbent structure 44 is free from securement to the outer cover 40 and the bodyside liner 42 within an inner region 124 of the central portion 112 in a manner similar to that described above and shown in FIG. 5. As additional examples, FIG. 8 illustrates the central portion 112 of the securement zone 102 as being generally V-shaped, or generally U-shaped, and FIG. 9 illustrates the central portion 112 of the securement zone 102 as being generally diamond shaped. In the embodiments illustrated in FIGS. 7–9, the length and width arrows (e.g., for the width $W_C$ and length $L_C$), are provided to illustrate the direction of and boundaries between which the measurement is taken and are not intended to indicate the location at which the average width or length as determined by the Securement Zone Measurement Method lies.

FIGS. 10 and 11 illustrate additional embodiments in which the pair of pants 220 has a generally hourglass configuration when laid flat whereby the width of the pants substantially narrows at the crotch region 226. The absorbent structure 244 also has an hourglass configuration wherein the width of the absorbent structure is substantially narrower at the crotch region 226 than at the front and back regions 222, 224 of the pants 220. The absorbent structure 244 is secured to the outer cover 240 and/or the bodyside liner 242 within a securement zone 302 extending longitudinally substantially the length of the absorbent structure. In FIG. 10, the securement zone 302 has a generally uniform width along the length thereof. Because of the narrow width of the absorbent structure 244 at the crotch region 226, the securement zone 302 is relatively wider at the crotch region (i.e., relative to the width of the absorbent structure) than at the front and back regions 222, 224.

For example, the side boundaries 308a, 308b of the securement zone 302 are within about 2.54 cm (about 1 inch) of the side edges of the absorbent structure 244 within the crotch region 226 of the pants 220 and the securement zone has a width that is at least about 20 percent of the width of the absorbent structure at the crotch region. At the front and back regions 222, 224 of the pants 220, the side boundaries 308a, 308b of the securement zone 302 are spaced from the side edges of the absorbent structure 244 a distance greater than about 2.54 cm (about 1 inch) and the securement zone has a width that is less than about 20 percent of the width of the absorbent structure at the respective front and back regions of the pants.

FIG. 11 is an embodiment similar to FIG. 10, but with a central portion 312 of the securement zone 302 being substantially wider than outer portions 314a, 314b thereof in a manner similar to the embodiments of FIGS. 4–9. More particularly, the central portion 312 of the securement zone 302 is generally hourglass shaped whereby the contour of the laterally opposite side boundaries 308a, 308b of the securement zone at the central portion thereof generally correspond to the contour of the absorbent structure side edges at the crotch region 226 of the absorbent structure. The wider central portion 312 of the securement zone 302 also defines longitudinal end boundaries 316a, 316b of the central portion spaced longitudinally inward of the longitudinal ends 310a, 310b of the securement zone. The dimensional relationships between the central portion 312 of the securement zone 302 and the absorbent structure 244, and between the outer portions 314a, 314b of the securement zone and the absorbent structure, are otherwise substantially as described previously for the embodiments of FIGS. 4–9.

SECUREMENT ZONE MEASUREMENT METHOD

The Securement Zone Measurement Method is used for locating the lateral side and longitudinal end boundaries 108a, 108b, 110a, 110b of the securement zone 102 (or boundaries 308a, 308b, 310a, 310b of the securement zone 302 of FIGS. 10 and 11) and for determining an average width and/or an average length of the securement zone or any portion thereof.

Five samples (e.g., five pants 20 or other absorbent article to be measured) are used to obtain the desired measurements and the results are averaged to determine the average widths and average lengths. To measure each sample, the sample is hung from a backlighting device having a flat illuminating backlit surface (not shown), otherwise sometimes referred to as a lightbox, in an unfolded, vertical orientation with one end (e.g., the front end) up and the outer cover 40 facing outward away from the light box. Thus, absorbent articles which are pre-packaged in a three-dimensional configuration must be unfastened or otherwise cut at the side seams thereof to unfold the article.

The backlighting device includes a pair of fixed upper clamps spaced laterally a distance corresponding to the maximum width $W_A$ of the absorbent structure 44. Where the sample has an elastic waistband at the front end thereof (e.g., such as is present at the front waist edge 38 of the pants 20 described herein), the waistband is generally fully stretched (e.g., to eliminate gathers in or otherwise straighten the waistband without stretching beyond what was originally gathered) and the clamps are clamped to the waistband without clamping any of the absorbent structure 44 therein. The sample is preferably secured to the clamps with the longitudinal axis 48 of the sample generally centered therebetween.

A clamp weight is then secured to the opposite (e.g., back) end of the sample so that the sample hangs freely from the upper clamps in a generally taut configuration but without substantially stretching the outer cover and bodyside liner of the sample. The clamp weight can be approximately 250 grams total mass (or whatever weight is needed to generally extend the sample without stretching) and includes a single weight held by a pair of clamps that are spaced apart at their centerlines the same distance as the clamps attached to the front end of the sample. Alternatively, two separate weights each weighing about 125 grams each can be held respectively by each of the clamps. As with the front end, where the back end of the sample has an elastic band (e.g., a waist band), the elastic band is generally fully stretched before the clamp weight is secured to the back end of the sample. Also, where the sample has longitudinally extending elastic components (e.g., such as the containment flap elastics 53 and leg elastic members 58 of the pants 20), it may be necessary to cut these elastic components (e.g., about every 2.5 cm) to allow the sample to hang freely. The tester then gently runs his or her fingers down the side edges of the sample to assure the sample is extended.

With the light in the backlighting device turned on, by sight and feel an outline of the absorbent structure 44 is determined and marked on the outer cover 40 of the sample with a suitable marker. A series of slits are then made in the outer cover 40 along the marked outline of the absorbent structure 44, with each slit being just wide enough to allow insertion therethrough of a 5 mm diameter probe measuring 10 cm to 30 cm in length. The probe may be made of stainless steel or other suitable material.

The probe is gently inserted generally horizontally through one of the slits and passed between the outer cover 40 and the absorbent structure 44 until resistance to further movement is encountered (thereby indicating an outermost location at which the absorbent structure 44 is secured to the outer cover 40). The location of the probe tip is then marked on the outer cover 40. The probe is then removed and sequentially inserted into each of the other slits and corresponding marks are made until the outline of the securement zone 102 between the outer cover 40 and the absorbent structure 44 becomes apparent. It may be necessary to repair a slit with cellophane or other tape before the next slit is made in order to keep the sample from falling apart under the tension created by the clamp weight.

The number of slits that need to be made is generally dependant on the complexity of the shape of the securement zone 102. For example, a simple uniform strip of adhesive down the center of the sample can be defined using relatively few slits because the edges of the adhesive pattern make a generally straight line. An adhesive pattern that has an oscillating boundary may take many slits that are close together, e.g., every one to two centimeters, to completely and accurately define the boundaries of the securement zone 102. The probings should be conducted in both the lateral and longitudinal directions in order to mark both lateral and longitudinal boundaries of the securement zone 102.

Where the absorbent structure is also secured to the liner 42 of the sample, the process is repeated with the sample mounted on the backlighting device so that the liner faces outward and the probe is instead inserted between the liner and the absorbent structure. Where the absorbent structure 44 is secured only to the liner 42, the measurement may be taken only on the liner side of the sample.

Using the absorbent structure outline and the probe markings, the lateral spacing of the securement zone from the side edges of the absorbent structure at a desired longitudinal position can be measured with a ruler. Likewise the average longitudinal distances $L_f$, $L_b$ of the end boundaries 116a, 116b of the central portion 112 of the securement zone 102 from the longitudinal ends of the sample can also measured with a ruler. The average width $W_C$ of the central portion 112 of the securement zone 102 is determined by measuring the lateral spacing between probe markings at at least five equally spaced longitudinal positions within the central portion of the securement zone and the results are averaged. The average width $W_O$ of each of the outer portions 114a, 114b of the securement zone 102 is measured in a similar manner. The average length $L_C$ of the central portion 112 of the securement zone 102 is determined by measuring the longitudinal distance (e.g., parallel to the longitudinal axis 48) between probe markings corresponding to the longitudinal end boundaries of the securement zone at at least five equally spaced locations across the width (e.g., on the lateral axis 49) of the central portion of the securement zone and the results are averaged.

When introducing elements of the present invention or the preferred embodiment(s) thereof, the articles "a", "an", "the", and "said" are intended to mean that there are one or more of the elements. The terms "comprising," "including", and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. An absorbent article having a longitudinal axis, a lateral axis, opposite longitudinal end regions and a central region extending longitudinally between and interconnecting the end regions, said absorbent article comprising:
    an outer cover;
    a bodyside liner adapted for contiguous relationship with the wearer's skin; and
    an absorbent structure disposed between the bodyside liner and the outer cover, the absorbent structure being secured to at least one of the liner and the outer cover within a securement zone, the securement zone comprising a central portion disposed generally within the central region of the article and having an average width as determined by a Securement Zone Measurement Method, and at least one outer portion disposed longitudinally outward of the central portion of the securement zone and having an average width as determined by the Securement Zone Measurement Method, said average width of the central portion of the securement zone being substantially greater than said average width of the at least one outer portion of said securement zone.

2. An absorbent article as set forth in claim 1 wherein the absorbent article has a length, the central portion of the securement zone having longitudinally opposite end boundaries defining an average length of said central portion as determined by said Securement Zone Measurement Method, said average length being in the range of about 5 percent to about 50 percent of the length of the absorbent article.

3. An absorbent article as set forth in claim 2 wherein the average length of the central portion of the securement zone is in the range of about 10 percent to about 30 percent of the length of the absorbent article.

4. An absorbent article as set forth in claim 3 wherein the average length of the central portion of the securement zone is in the range of about 10 percent to about 20 percent of the length of the absorbent article.

5. An absorbent article as set forth in claim 1 wherein the absorbent article has a length, the central portion of the securement zone having longitudinally opposite end boundaries, one of said end boundaries being spaced from a respective end of the absorbent article a distance in the range of about 20 percent to about 45 percent of the length of the absorbent article, the opposite end boundary of the central portion of the securement zone being longitudinally spaced from the respective opposite end of the absorbent article a distance in the range of about 20 percent to about 50 percent of the length of the absorbent article.

6. An absorbent article as set forth in claim 1 wherein the absorbent structure is secured to said at least one of the outer cover and the bodyside liner with adhesive.

7. An absorbent article as set forth in claim 6 wherein the adhesive is a meltblown adhesive.

8. An absorbent article as set forth in claim 1 wherein the securement zone comprises a pair of outer portions extending longitudinally outward of the central portion of said securement zone, one of said outer portions extending longitudinally toward one end of the absorbent article, the other outer portion extending longitudinally toward the opposite end of the absorbent article.

9. An absorbent article as set forth in claim 1 wherein the absorbent structure has laterally opposite side edges, the securement zone having laterally opposite side boundaries, the side boundaries of the securement zone at the central portion thereof being disposed laterally within at least about one inch (2.54 centimeters) of the respective side edges of the absorbent structure at the central portion of the securement zone, the side boundaries of the securement zone at said at least one outer portion thereof being spaced laterally inward of the respective side edges of the absorbent structure at the said least one outer portion of the securement zone a distance greater than about one inch (2.54 centimeters).

10. An absorbent structure as set forth in claim 1 wherein said average width of the central portion of the securement zone is at least about 20 percent of the width of the absorbent structure at said central portion of the securement zone, said average width of said at least one outer portion of the securement zone being less than about 20 percent of the width of the absorbent structure at said at least one outer portion.

11. An absorbent structure as set forth in claim 10 wherein said average width of the central portion of the securement zone is in the range of about 20 percent to about 80 percent of the width of the absorbent structure at said central portion of the securement zone.

12. An absorbent structure as set forth in claim 10 wherein said average width of the central portion of the securement zone is in the range of about 20 percent to about 60 percent of the width of the absorbent structure at said central portion of the securement zone.

13. An absorbent structure as set forth in claim 1 wherein the absorbent structure is secured to both the outer cover and the bodyside liner within the securement zone.

14. An absorbent article as set forth in claim 1 wherein at least one of the outer cover and the bodyside liner is stretchable.

15. An absorbent article as set forth in claim 14 wherein said at least one of the outer cover and the bodyside liner is elastic.

16. An absorbent article as set forth in claim 14 wherein the absorbent structure is substantially non-stretchable.

17. An absorbent article as set forth in claim 1 wherein the securement zone extends continuously generally from within one end region of said article through the central region to within the opposite end region of said article.

18. An absorbent article as set forth in claim 1 wherein the absorbent article has longitudinally opposite ends, the central portion of the securement zone being disposed nearer to one end of the article than to said opposite end of said article.

* * * * *